United States Patent
Akbari et al.

(10) Patent No.: US 12,390,653 B2
(45) Date of Patent: Aug. 19, 2025

(54) SPREADING DEPOLARIZATION AND REPOLARIZATION AS BIOMARKERS OF NEUROLOGICAL RECOVERY AFTER CARDIAC ARREST

(71) Applicant: THE REGENTS OF THE UNIVERSITY OF CALIFORNIA, Oakland, CA (US)

(72) Inventors: Yama Akbari, Irvine, CA (US); Robert H. Wilson, Irvine, CA (US); Christian Crouzet, Irvine, CA (US); Bernard Choi, Irvine, CA (US); Bruce J. Tromberg, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 869 days.

(21) Appl. No.: 17/277,616

(22) PCT Filed: Sep. 23, 2019

(86) PCT No.: PCT/US2019/052486
§ 371 (c)(1),
(2) Date: Mar. 18, 2021

(87) PCT Pub. No.: WO2020/061576
PCT Pub. Date: Mar. 26, 2020

(65) Prior Publication Data
US 2022/0032074 A1 Feb. 3, 2022

Related U.S. Application Data

(60) Provisional application No. 62/734,417, filed on Sep. 21, 2018.

(51) Int. Cl.
*A61N 1/39* (2006.01)
*A61B 5/00* (2006.01)
(Continued)

(52) U.S. Cl.
CPC ........... *A61N 1/39044* (2017.08); *A61B 5/37* (2021.01); *A61B 5/4839* (2013.01);
(Continued)

(58) Field of Classification Search
None
See application file for complete search history.

(56) References Cited

U.S. PATENT DOCUMENTS

| | | |
|---|---|---|
| 4,709,702 A | 12/1987 | Sherwin |
| D739,122 S | 9/2015 | Aimone et al. |

(Continued)

FOREIGN PATENT DOCUMENTS

| | | | |
|---|---|---|---|
| DE | 10153360 A1 | 10/2001 | |
| EP | 3020333 A1 * | 5/2016 | ......... A61B 5/04014 |

(Continued)

OTHER PUBLICATIONS

H. Adrian Puttgen and Romergryko Geocadin, "Predicting neurological outcome following cardiac arrest", Journal of the Neurological Sciences 261 (2007) pp. 108-117 (Year: 2007).*
(Continued)

*Primary Examiner* — Daniel L Cerioni
*Assistant Examiner* — Om Patel
(74) *Attorney, Agent, or Firm* — NGUYEN TARBET IP LAW

(57) ABSTRACT

Electrophysiologic biomarkers for prognostication of neurological outcome are described herein. An inverse correlation was found between timing of a cortical spreading depolarization (SD) wave and neurological outcome as tested at 24 hours post-CPR. Additionally, a minor image of this SD was identified as a "repolarization (RP) wave." Quantifying features of SD and RP during cardiac arrest and cardiopulmonary resuscitation (CPR) provide important metrics for diagnosis and prognosis of neurological injury (Continued)

from hypoxia-ischemia and can serve as an early prognostication tool for predicting outcome at subsequent days after successful CPR. This discovery may also allow for novel therapeutic interventions to improve neurological recovery after hypoxia-ischemia insults.

7 Claims, 15 Drawing Sheets
(15 of 15 Drawing Sheet(s) Filed in Color)

(51) Int. Cl.
*A61B 5/026* (2006.01)
*A61B 5/37* (2021.01)
*A61H 31/00* (2006.01)

(52) U.S. Cl.
CPC .......... *A61H 31/005* (2013.01); *A61B 5/0261* (2013.01); *A61H 2201/5094* (2013.01); *A61H 2230/085* (2013.01); *A61H 2230/105* (2013.01); *A61H 2230/255* (2013.01)

(56) References Cited

U.S. PATENT DOCUMENTS

| | | | |
|---|---|---|---|
| 9,730,649 | B1 | 8/2017 | Jepsen |
| 10,009,644 | B2 | 6/2018 | Aimone et al. |
| 10,321,842 | B2 | 6/2019 | Garten et al. |
| 2004/0068199 | A1 | 4/2004 | Echauz et al. |
| 2005/0143589 | A1 | 6/2005 | Donoghue et al. |
| 2006/0281983 | A1 | 12/2006 | Al-Ali et al. |
| 2007/0191689 | A1 | 8/2007 | Elitok |
| 2008/0177572 | A1 | 7/2008 | Fuhrman et al. |
| 2008/0243022 | A1* | 10/2008 | Donnett ................. A61B 5/372 600/544 |
| 2008/0249430 | A1* | 10/2008 | John ....................... A61B 5/372 600/544 |
| 2009/0118622 | A1 | 5/2009 | Durkin et al. |
| 2010/0241100 | A1 | 9/2010 | Blumenfeld et al. |
| 2011/0105912 | A1 | 5/2011 | Widman et al. |
| 2012/0143020 | A1 | 6/2012 | Bordoley et al. |
| 2013/0261183 | A1 | 10/2013 | Bhagat |
| 2014/0018649 | A1 | 1/2014 | Jespersen et al. |
| 2014/0088996 | A1 | 3/2014 | Damani |
| 2015/0051521 | A1 | 2/2015 | Woerlee et al. |
| 2015/0257674 | A1 | 9/2015 | Jordan et al. |
| 2016/0317385 | A1 | 11/2016 | Salcido et al. |
| 2016/0345880 | A1 | 12/2016 | Nakaji et al. |
| 2017/0135594 | A1 | 5/2017 | Hartings et al. |
| 2017/0224246 | A1* | 8/2017 | Jiang ...................... A61B 5/725 |
| 2018/0044278 | A1 | 2/2018 | Bazan et al. |
| 2018/0085047 | A1 | 3/2018 | Hartings et al. |
| 2018/0246570 | A1 | 8/2018 | Coleman et al. |
| 2018/0308390 | A1 | 10/2018 | Moser et al. |
| 2019/0053721 | A1 | 2/2019 | Boas et al. |
| 2019/0113973 | A1 | 4/2019 | Coleman et al. |
| 2019/0117500 | A1 | 4/2019 | Shaw et al. |
| 2019/0159675 | A1 | 5/2019 | Sengupta et al. |
| 2019/0306438 | A1 | 10/2019 | Regan et al. |
| 2019/0306439 | A1 | 10/2019 | Morales Delgado et al. |
| 2019/0384392 | A1 | 12/2019 | Aimone et al. |
| 2020/0019243 | A1 | 1/2020 | Aimone et al. |

FOREIGN PATENT DOCUMENTS

| | | |
|---|---|---|
| WO | WO2008109699 A2 | 12/2008 |
| WO | WO2016164891 A1 | 10/2016 |
| WO | WO2020243658 A1 | 12/2020 |

OTHER PUBLICATIONS

Andy Temple, Richard Porter, Predicting neurological outcome and survival after cardiac arrest, Continuing Education in Anaesthesia Critical Care & Pain, vol. 12, Issue 6, Dec. 2012, pp. 283-287 (Year: 2012).*

Jens P. Dreier, Coline L. Lemale, Vasilis Kola, Alon Friedman, Karl Schoknecht, Spreading depolarization is not an epiphenomenon but the principal mechanism of the cytotoxic edema in various gray matter structures of the brain during stroke, Neuropharmacology, vol. 134, Part B, 2018, pp. 189-207 (Year: 2018).*

Nicolas Lellouche, Frederic Sacher, Pierre Jorrot, Alain Cariou, Christian Spaulding, et al.. Sudden Cardiac Arrest: ECG Repolarization After Resuscitation . . . Journal of Cardiovascular Electrophysiology, 2011, 22 (2), pp. 131-1366 (Year: 2011).*

Salvo et al. A 3D printed dry electrode for ECG/EEG recording, Sensors and Actuators A: Physical, Dec. 8, 2011, p. 96-102, Elsevie B.V.

Wiebe et al. EEG-PEN for Medical Emergencies, Biomedical Engineering / Biomedizinische Technik Oct. 23, 2009, vol. 47, Issue s1a, DOI: https://doi.org/10.1515/bmte.2002.47.s1a.308.

Krachunov et al. 3D Printed Dry Electrodes, Sensors Journal, 1635, pp. 1-18, Oct. 2, 2016 doi:10.3390/s16101635.

Cuccia et al. "Quantitation and mapping of tissue optical properties using modulated imaging." Journal of biomedical optics 14.2 (2009): 024012.

Dreier et al. "Spreading depolarization is not an epiphenomenon but the principal mechanism of the cytotoxic edema in various gray matter structures of the brain during stroke." Neuropharmacology 134 (2018): 189-207.

* cited by examiner

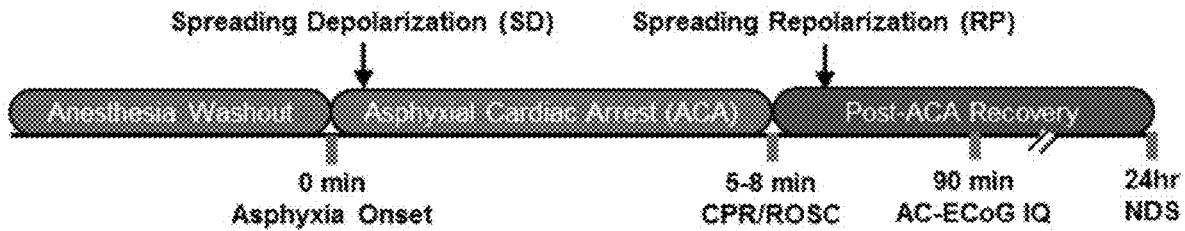

FIG. 1E

Neurological Deficit Scale (NDS) for Rats

*Arousal (0-19)*

Alerting — Normal (10); Stuporous (5); Comatose (0)

Eye Opening — Open spontaneous (3); Open to pain (1)

Spontaneous Respiration — Normal (6); Abnormal (3); Absent (0)

*Brainstem Function (0-21)*

For each category: Normal (3); Abnormal (1); Absent (0)

Olfaction; Vision; Pupillary Light Reflection; Corneal Reflex; Startle Reflex; Whisker Stimulation; Swallowing

*Motor Assessment (0-6)*

Strength — Normal (3); Weak (1); No movement (0)

*Sensory Assessment (0-6)*

Pain — Brisk (3); Weak (1); No movement (0)

*Motor Behavior (0-6)*

For each category: Normal (3); Abnormal (1); Absent (0)

Gait Coordination; Balance Beam Walking

*Behavior (0-12)*

For each category: Normal (3); Abnormal (1); Absent (0)

Right Reflex; Visual Placing; Negative Geotaxis; Turning Alley

Best Outcome = 70; Worst Outcome = 0

FIG. 1F

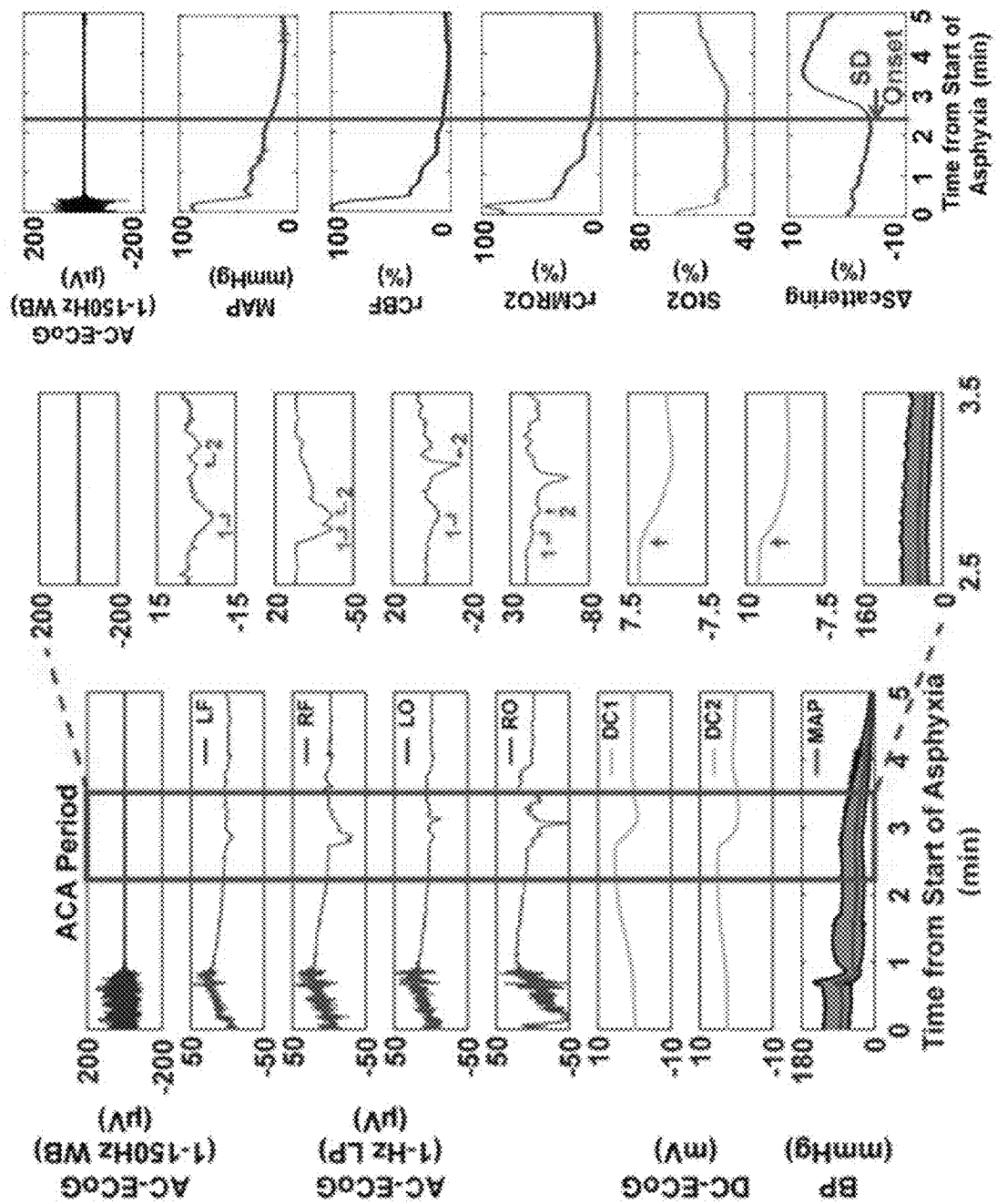
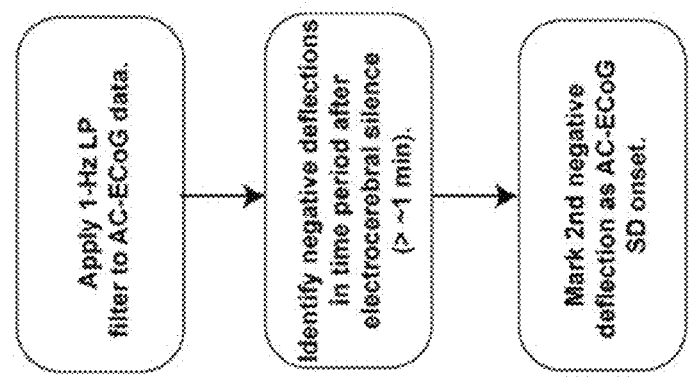
FIG. 2A
FIG. 2B
FIG. 2C

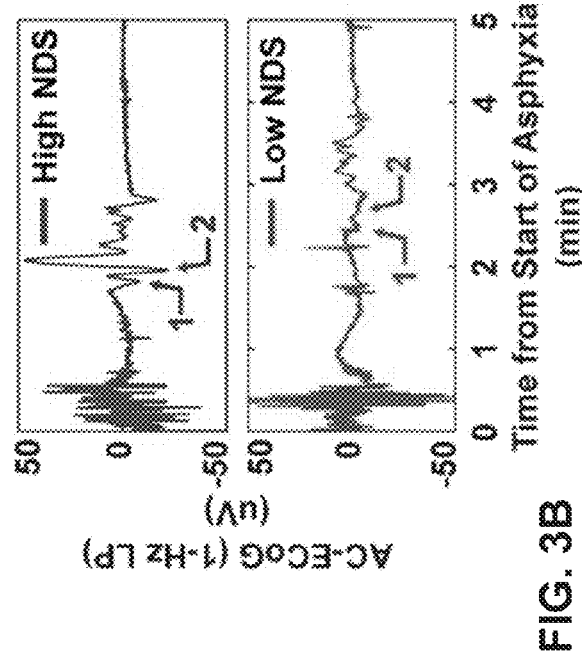
FIG. 3A
FIG. 3B
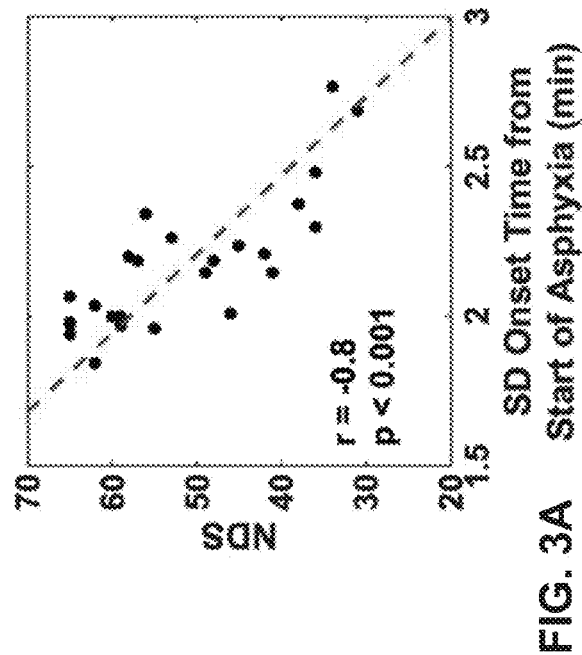
FIG. 3C
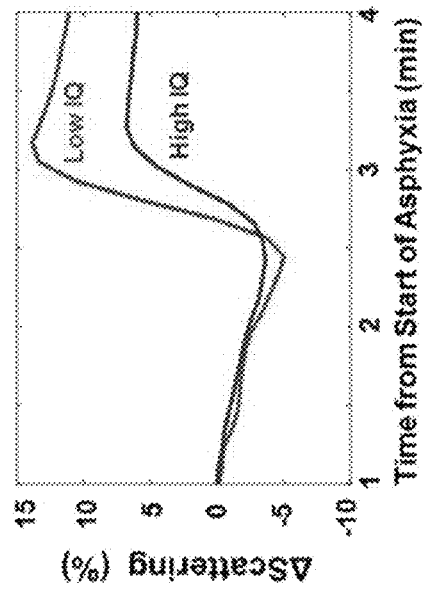
FIG. 3D
FIG. 3E
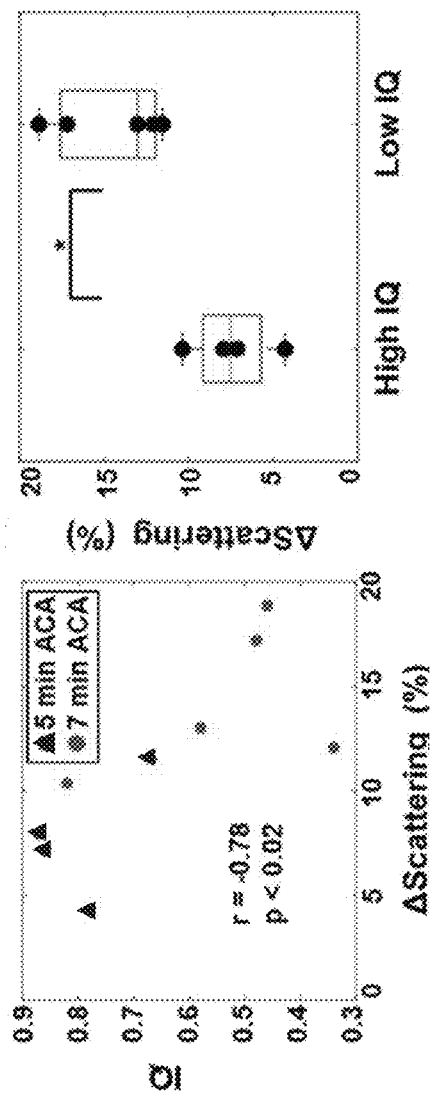

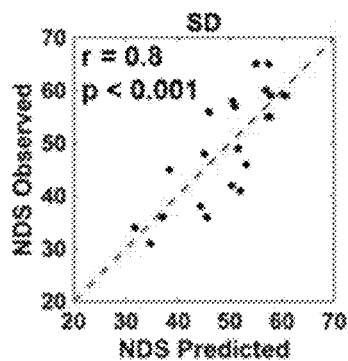
FIG. 7A
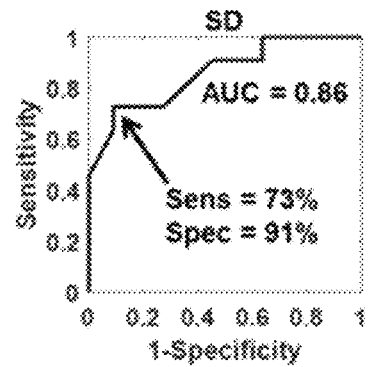
FIG. 7B
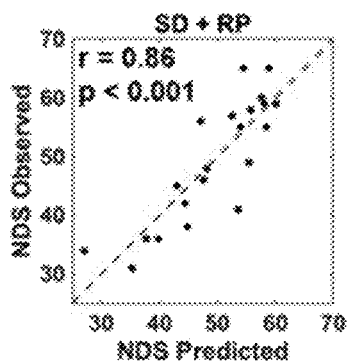
FIG. 7C
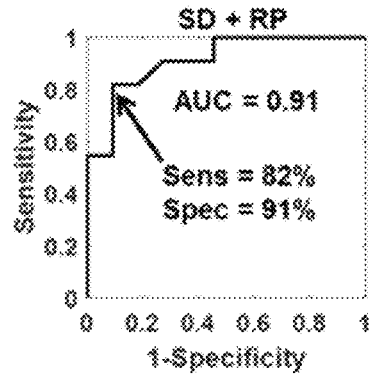
FIG. 7D
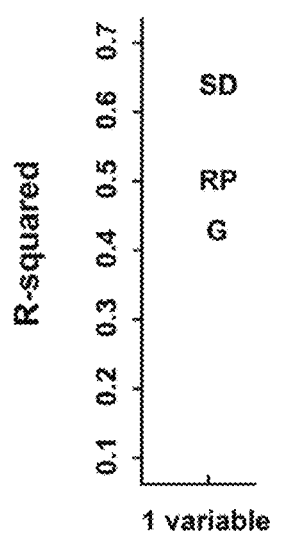
FIG. 8A
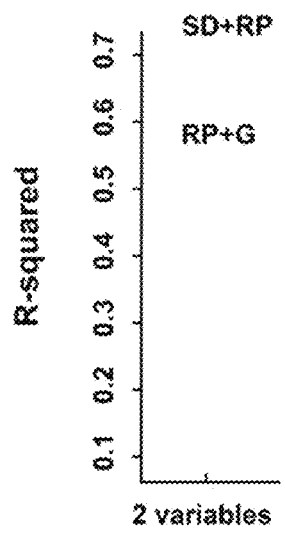
FIG. 8B
FIG. 8C
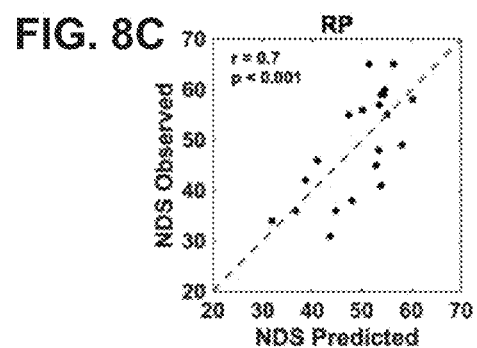
FIG. 8D
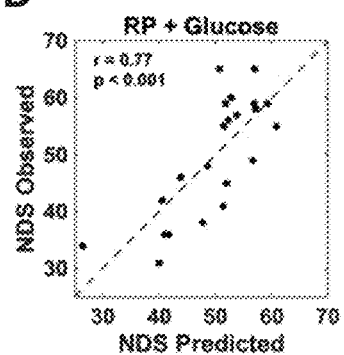

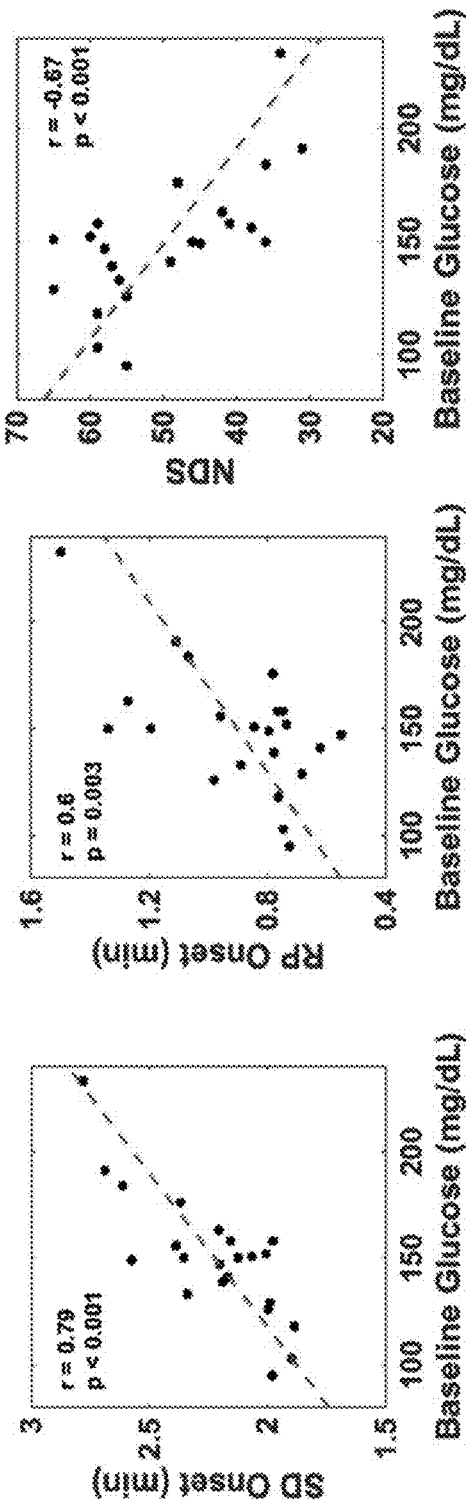
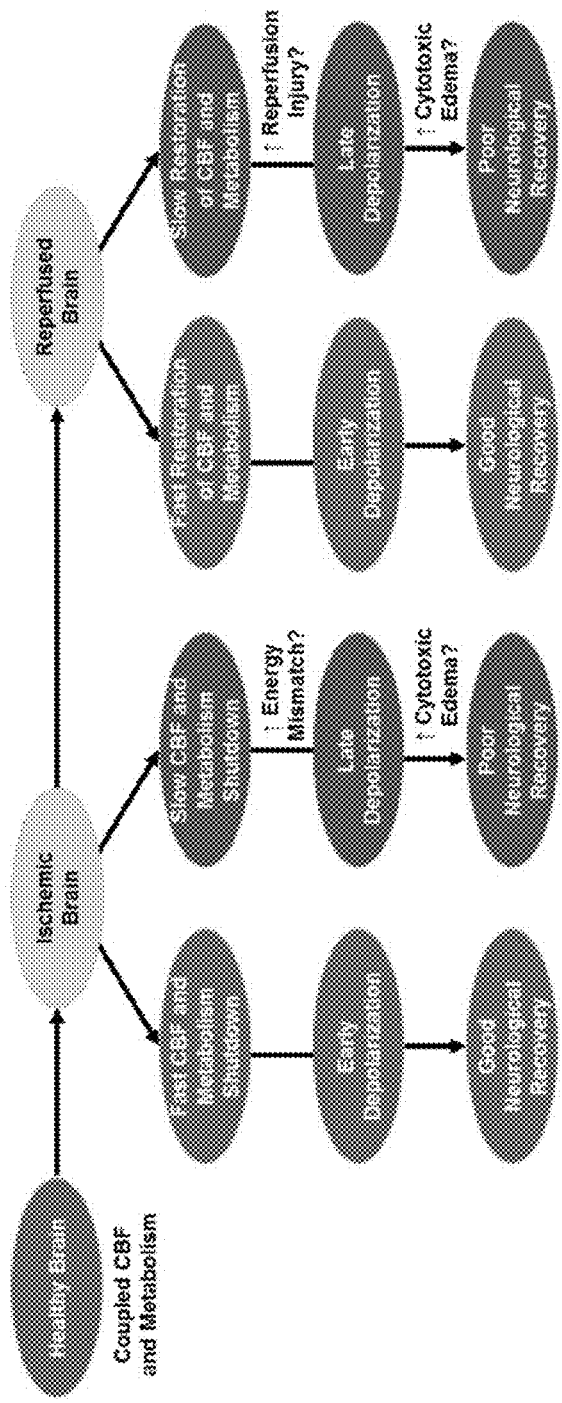

SPREADING DEPOLARIZATION AND REPOLARIZATION AS BIOMARKERS OF NEUROLOGICAL RECOVERY AFTER CARDIAC ARREST

CROSS-REFERENCES TO RELATED APPLICATIONS

This application claims benefit of U.S. Provisional Application No. 62/734,417 filed Sep. 21, 2018, the specification(s) of which is/are incorporated herein in their entirety by reference.

GOVERNMENT SUPPORT

This invention was made with government support under Grant Nos. KL2 TR000147, R21 EB024793, and UL1 TR001414 awarded by NIH. The government has certain rights in the invention.

FIELD OF THE INVENTION

The present invention relates to electrophysiological and optical monitoring of the brain, namely, detection of either an electrical signal or an optical signal that can serve as a biomarker for neurological outcome after cardiac arrest-induced brain ischemia with potential therapeutic potential.

BACKGROUND OF THE INVENTION

Cardiac arrest (CA) afflicts over half a million individuals in the USA annually with costs to society ranging close to $50 billion per year. Survival rates have remained abysmal over the past few decades with only 5-11% of out-of-hospital and ~17% of in-hospital CA sufferers surviving. Almost 90% of CA survivors emerge in a comatose state with severe neurological damage needing significant medical care. After cardiopulmonary resuscitation (CPR), neurologic outcome is poor because devastating hypoxic-ischemic damage to the brain has already occurred.

Predicting outcome after cardiac arrest is important to allow decision-making by family members and direction of care by health care professionals. A variety of prognosticative approaches have been studied to stratify likelihood of patients emerging from a comatose or vegetative state to an awake and responsive state. These approaches to prognostication have included pre-cardiac arrest risk factors, intra-cardiac arrest parameters, and post-cardiac arrest factors. The earlier a prognostic tool is available, the more information is available to clinicians and family members to help with decision-making, including whether to pursue life-saving measures requiring prolonged life support, or whether to allow the patient to pass away in dignity without prolonging suffering with little hope of a meaningful recovery. Thus, having the earliest possible prognostication tool can help guide optimal resuscitation measures during the cardiac arrest as well as during post-resuscitation treatments.

Currently, the main information during a cardiac arrest that is helpful for prognostication is the type of cardiac arrest (shockable or non-shockable rhythm) and the duration of cardiac arrest before resuscitation efforts have begun. For example, knowing that a patient has suffered a very prolonged cardiac arrest in a non-shockable state forebodes a very poor prognosis, whereas if help and resuscitation starts within seconds or <5 minutes after a cardiac arrest (especially a shockable rhythm), there is a meaningful chance of a good recovery if resuscitation is successful. The latter would encourage clinicians and family to continue full life support and treatment since hope can be maintained of a positive outcome. While there are some prognostic tools during resuscitation efforts, such as the quality of CPR as relayed by end-tidal carbon dioxide ($CO_2$) levels, some of these tools may not be available in certain settings.

Finally, after resuscitation, the main tools available for prognostication are neurological exams, brain imaging (CT, MRI), electrophysiologic testing such as electroencephalography (EEG) and somatosensory evoked potentials (SSEP), and blood tests (e.g. neuron-specific enolase (NSE)). However, these tests only provide value many hours or days (e.g. 24-72 hours) after successful resuscitation and many of the processes responsible for ischemic damage and reperfusion injury in the brain are well-underway by the time that these exams are completed. No test is available immediately after resuscitation to help prognostication occur early on. Moreover, many tools have high false positive rates or false negative rates that unreliably predict outcome. Hence, novel discoveries for early prognostication that serve as a handle for treatments to allow for harnessing of the mechanisms underlying the prognostic tool are desired.

Spreading depolarization (SD) is a self-propagating wave of neuronal depolarization that results in cytotoxic edema of neurons. With an inability to maintain membrane potential, SD marks near complete loss of neuronal activity in energy-compromised tissue. SD-related phenomena are seen in a multitude of conditions including migraine aura, traumatic brain injury, hypoxia, ischemia, as well as experimental manipulations such as administration of KCI directly onto the brain. Ischemia-induced SD results in the morphological alteration of neurons, including damage to dendritic spines. This "wave of death" has been shown to mark the onset of cytotoxic events (e.g., glutamate release, $Ca^{2+}$ influx, cytotoxic edema), however, this damage can be reversed with timely reperfusion. Further still, SD is particularly harmful to brain parenchyma and cerebral vasculature in a hypoxic/ischemic state, like that which occurs during cardiac arrest. With no intervention, CA results in terminal spreading depolarization. Quantifying SD during CA and resuscitation may provide an important tool for diagnosis, prognosis, and possible therapeutic interventions during neurological injury during hypoxic-ischemic events. Furthermore, there remains a critical need for rapid prognostic tools to guide novel therapeutic strategies at ultra-early time points during CA and immediately following resuscitation.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

Cardiac arrest (CA) affects >550,000 people annually in the USA, with the vast majority dying or surviving with severe neurological deficits. Prognostication after CA and cardiopulmonary resuscitation (CPR) is important to help determine goals of care and course of treatment. Current prognostic tests for neurological outcome include the bedside neurological exam, neurophysiologic testing (EEG, SSEPs), brain imaging (CT, MRI), and blood testing (NSE) hours or days post-CPR. Here, the present invention focuses on the role of spreading depolarizations (SD) in CA and post-CPR. The invention utilized a multimodal electrophysiological and optical platform to investigate brain injury, including global cerebral ischemia and reperfusion during CA and CPR.

In some aspects, the present invention features a system for monitoring and determining neurological outcome of a brain post cardiac arrest (CA). The system may comprise an electrophysiological monitoring device for detecting spreading depolarization (SD) and repolarization (RP) in the brain, one or more optical measurement devices for measuring cerebral blood flow (CBF), tissue oxygenation, and/or tissue scattering in the brain, a processor operatively coupled to the electrophysiological monitoring device and the one or more optical measurement devices, and a memory coupled to the processor. The one or more optical measurement devices may also detect SD and RP.

The memory stores a one or more metrics for determining a neurological outcome score, as well as computer-readable instructions that, when executed by the processor, causes the processor to perform operations. These operations include receiving SD and RP data from the electrophysiological monitoring device and/or the one or more optical measurement devices, receiving measurements of CBF, tissue oxygenation, and/or tissue scattering from the one or more optical measurement devices, determining cerebral metabolic rate of oxygen (CMRO2) from the measurements of CBF and tissue oxygenation, determining tissue scattering change onset, duration, and magnitude from the tissue scattering measurements, comparing the SD and RP data, CMRO2, scattering change onset, scattering change duration, scattering change magnitude, CBF, and tissue oxygenation measurements to the plurality of metrics to determine an estimated neurological outcome score, and identifying a neurological condition of the brain based on the neurological outcome score.

In some embodiments, the one or more optical measurement devices may comprise a point measurement device, diffuse optical measurement including, but not limited to, near-infrared spectroscopy (NIRS) based devices, or optical measurement devices that can measure CBF, tissue oxygenation, and/or tissue scattering through intact human skull. In other embodiments, the electrophysiological monitoring device comprises a plurality of electrodes operatively coupled to a detector, such as EEG or ECoG. In yet other embodiments, the plurality of metrics are based on measures of neurological status or outcome, including but not limited to a Glasgow Coma Scale (GCS), Cerebral Performance Category (CPC), a Modified Rankin Scale (mRS), or specific features of a neurological exam.

In one embodiment, the system may further comprise a means for inducing SD in the brain. For example, the means for inducing SD or RP may comprise chemical stimulation, physical stimulation, electrical stimulation, magnetic stimulation, optical stimulation, soundwave-induced stimulation, or a combination thereof. In another embodiment, the system may include a means for inducing RP in the brain, such as chemical stimulation, physical stimulation, electrical stimulation, magnetic stimulation, optical stimulation, soundwave-induced stimulation, or a combination thereof.

According to other aspects, the present invention features a method of improving neurological outcome in a subject during cardiac arrest. The method may comprise detecting spreading depolarization (SD), or a lack or delay thereof, in a brain of the subject post cardiac arrest, detecting repolarization (RP), or a lack or delay thereof, in the brain of the subject post resuscitation, measuring cerebral blood flow (CBF), tissue oxygenation, and tissue scattering in the brain, determining cerebral metabolic rate of oxygen (CMRO2) from the measurements of CBF and tissue oxygenation, determining scattering change onset, duration, and magnitude from the tissue scattering measurements, comparing SD and RP data, CMRO2, scattering change onset, scattering change duration, scattering change magnitude, CBF, and tissue oxygenation measurements to a plurality of metrics to determine an estimated neurological outcome score, identifying a neurological condition of the brain based on the neurological outcome score, and administering a treatment to the subject to improve the neurological condition of the brain. Examples of treatments include, but are not limited to, therapeutically administering a drug, electrical stimulation, magnetic stimulation, optical stimulation, soundwave-induced stimulation, or a combination thereof.

In one embodiment, cerebral blood flow (CBF), tissue oxygenation, and/or tissue scattering are measured by one or more optical measurement devices comprising point measurement devices, diffuse optical measurement devices such as NIRS, or optical measurement devices that measure CBF, tissue oxygenation, and/or tissue scattering through intact human skull. In another embodiment, SD and RP may be detected by electrode-based devices, such as EEG or an ECoG, and/or the one or more optical measurement devices.

In some embodiments, SD may not be detected, e.g. SD may not occur or it may be delayed after a specific period of time. If SD is not detected or if it is expected to be delayed, prognosing poor outcome, SD can be induced earlier to improve neurological outcome. In other embodiments, RP may not be detected. For instance, RP may not have occurred or it may be delayed after a period of time. If RP is not detected or if it is expected to be delayed, prognosing poor outcome, RP can be induced earlier to improve neurological outcome. Thus, a lack or delay of SD or RP may indicate that SD or RP should be induced in the patient. In some embodiments, the methods described herein may further comprise inducing SD in the brain during or immediately after cardiac arrest. In other embodiments, the method may further comprise inducing RP in the brain during or immediately after resuscitation. Methods of inducing SD or RP include chemical stimulation, physical stimulation, electrical stimulation, magnetic stimulation, optical stimulation, soundwave-induced stimulation, or a combination thereof. In some embodiments, treatments for improving neurological outcome are based on inducing SD and/or RP promptly. If SD and/or RP is already detected, then SD and/or RP may not need to be induced, e.g. detection is only for prognosing.

In preferred embodiments, the systems and methods of the present invention can gauge severity and prognosticate outcome of the neurological condition of the brain in real-time. Without wishing to limit the present invention, the inventors have surprisingly found that SD and RP are biomarkers for neurological outcome post-cardiac arrest and resuscitation, respectively. In one embodiment, earlier onsets of SD and RP may be indicative improved neurological outcome. In another embodiment, the onset of SD that is indicative of improved neurological outcome falls within a time range of about 1.4 minutes to about 2.5 minutes after initiation of a brain insult or a global bodily insult that can affect the brain. In yet another embodiment, the onset of RP that is indicative of improved neurological outcome falls within a time range of about 0.25 minutes to about 2 minutes after restoration of spontaneous circulation following a brain insult or a global bodily insult that can affect the brain. The brain insult or global insult includes, but is not limited to, asphyxia/anoxia onset or severe progressive hypotension leading to non-shockable cardiac arrest in the form of pulseless electrical activity, shockable cardiac arrest (e.g. ventricular fibrillation or unstable ventricular tachycardia), or non-shockable cardiac arrest in the form of asystole.

In the present invention, a preclinical model of asphyxial CA (ACA) and CPR, along with an electrocorticography (ECoG) and optical measurement platform, was used to characterize SD during ACA and repolarization (RP) post-CPR. While SD has been studied for many decades and has been identified in the hypoxic or ischemic brain, to date, no one has explored it for prognostication of outcome. Additionally, the vast majority of literature suggests that SDs are harmful to the brain. The inventors have found a strong inverse correlation between timing of the SD wave and the neurological outcome as tested at 24 hours post-CPR. Additionally, the inventors have identified the mirror image of this SD, which is an RP wave. On EEG/ECoG and DC electrophysiology recordings, this RP wave after resuscitation and reperfusion can be seen as a rise in the voltage during these electrophysiology techniques, which is opposite in direction as the depolarization wave seen during cardiac arrest, hence appearing like a mirror image of it. The statistical analysis shows that SD and the RP wave in animals can serve as a prognostication tool for outcome at subsequent days after successful CPR. Without wishing to be bound to a particular theory, earlier SD and earlier RP may be associated with better neurological outcome. Further, the present invention has therapeutic implications: If the energy of CSD can be harnessed and induced earlier during cardiac arrest, this may lead to improved outcomes.

Since the current arts suggest that SD is harmful to the brain and exacerbates ischemic brain injury, the inventors had initially hypothesized that resilience to SD, marked by delayed onset of SD during ischemic events, may be associated with better neurological outcome after cardiac reperfusion. However, the inventors surprisingly discovered that earlier onset of SD may be indeed associated with better neurological outcome after cardiac reperfusion.

BRIEF DESCRIPTION OF THE DRAWINGS

The patent application or application file contains at least one drawing executed in color. Copies of this patent or patent application publication with color drawing(s) will be provided by the Office upon request and payment of the necessary fee. The features and advantages of the present invention will become apparent from a consideration of the following detailed description presented in connection with the accompanying drawings in which:

FIG. 1E shows a timeline of ACA and CPR experiment. Isoflurane anesthesia is washed out over 3 min, during which a neuromuscular blocker (vecuronium) is administered. ACA is induced by turning off the ventilator for a 5-8 min asphyxial period, depending on experimental cohort. CPR is administered until return of spontaneous circulation (ROSC). Neurological outcome is determined by 24-hr post-ROSC neurological deficit score (NDS) testing or 90-min post-ROSC alternating current electrocorticography (AC-ECoG) information quantity (IQ). As used herein, IQ is a measure of entropy on the ECoG signal that is a surrogate marker of neurological recovery, with higher IQ close to the baseline (pre-ACA) signifying better neurological recovery and lower IQ signifying worse neurological recovery.

FIG. 1F shows an example of a Neurological Deficit Scale (NDS). Various behaviors and reflexes are scored in order to assess neurological recovery in post-ACA rodents. NDS performance ranges from 70 (best score) to 0 (worst score).

FIG. 2A is a flow diagram for detecting and characterizing spatiotemporal features of SD during ACA with multiple measurement modalities.

FIG. 2B shows results of DC-ECoG in Cohort 2. SD from ACA appears as an ultra-slow wave in 1-Hz low-pass (LP) AC-ECoG in Cohorts 1 and 2 for 8-min ACA. This feature is not visible in 1-150 Hz wide-band (WB) AC-ECoG. SD occurs after electrocerebral silence. SD onset for each channel (LF=left frontal; RF=right frontal; LO=left occipital; RO=right occipital) was marked manually on 1-Hz LP AC-ECoG traces in Cohort 1 by the $2^{nd}$ negative deflection. The arrows and numbers denote the $1^{st}$ and $2^{nd}$ negative deflections.

FIG. 2C shows a gradual decrease and subsequent rapid increase in tissue scattering, attributed to cytotoxic edema and dendritic beading, observed during SD. In addition, an upward deflection in tissue oxygenation ($StO_2$), attributed to cessation of metabolism, is observed immediately following SD. Onset of SD, as defined by onset of spatial propagation of tissue scattering change in optical imaging window, is denoted by the gray vertical line. rCBF and rCMRO2 denote changes relative to pre-asphyxia baseline in CBF and CMRO2.

FIG. 3A is a graph of SD onset and neurological outcome (NDS). Earlier LP AC-ECoG SD onset is associated with better NDS in Cohort 1.

FIG. 3B show representative 1-Hz LP AC-ECoG tracings indicating earlier SD onset for a rat with good NDS (NDS≥49) and later onset for a rat with poor NDS (NDS<49). Delayed SD onset and increased cytotoxic edema are associated with poor outcome FIG. 3C is a graph of Δscattering and IQ where smaller increases in tissue scattering during SD are associated with higher AC-ECoG IQ post-ROSC.

FIG. 3D show Δscattering for high IQ and low IQ, where rats with low IQ exhibit larger increases in tissue scattering.

FIG. 3E shows representative tissue scattering tracings having greater increase in tissue scattering for a rat with low IQ.

In FIGS. 4A-4D, reduced total (AUC; area under the curve) mean arterial pressure (MAP) and cerebral blood flow (CBF) during entry into CA (asphyxia up to SD onset) are associated with better neurological recovery (24-hr NDS, FIG. 4A; ECoG IQ 90 min post-ROSC, FIG. 4C). In FIGS. 4E-4G, lower cerebral perfusion/metabolism ratio (CBF/CMRO2) at SD onset is associated with higher IQ. In FIG. 4H, rats with high IQ also have lower ratio of total cerebral perfusion (CBF AUC) to total cerebral metabolism (CMRO2 AUC) over the period from start of asphyxia to SD onset.

In FIG. 6A, for Cohort 1, more total MAP, from ROSC until RP onset, trends toward worse neurological outcome (NDS). In FIG. 6B, for Cohort 3, high IQ rats have significantly less total MAP from ROSC until RP. In FIGS. 6C-6F, high IQ rats also have significantly less cerebral reperfusion and metabolism from ROSC until RP.

FIGS. 7A-7D show a neurological outcome prediction model with SD and RP onsets. Out of 13 variables for Cohort 1, SD onset in FIG. 7A predicted NDS with greatest accuracy in models using 1 predictor variable (r=0.8; ROC AUC=0.86). In FIG. 7B, optimal sensitivity and specificity, as determined by Youden's J statistic, were 73% and 91%, respectively. In FIG. 7C, adding RP onset as a second predictor variable improved the accuracy of the model (r=0.86; ROC AUC=0.91). In FIG. 7D, optimal sensitivity and specificity, as determined by Youden's J statistic, were 82% and 91%, respectively.

FIGS. 8A-8D show correlations between linear regression model and NDS. In FIG. 8A, SD onset, RP onset, and baseline glucose in Cohort 1 provided the strongest correlations for 1 predictor models. In FIG. 8B, the RP onset predictor model was significantly improved with addition of baseline glucose. Five rats were removed from prediction model formulation to match number of RP onset values (n=22). G=baseline glucose. FIG. 8C shows predicted NDS using RP onset alone correlated with true NDS (r=0.7). FIG. 8D shows predicted NDS using RP onset +glucose provided an improved correlation with true NDS (r=0.77), relative to RP onset alone.

FIGS. 9A-9C show baseline glucose correlations with SD onset, RP onset, and NDS, respectively.

FIG. 10 is a flow chart outlining associations between SD, RP, and neurological outcome. Early SD and RP are associated with good neurological outcome, while delayed SD and RP are associated with poor neurological outcome

DESCRIPTION OF PREFERRED EMBODIMENTS

Figure 1A:
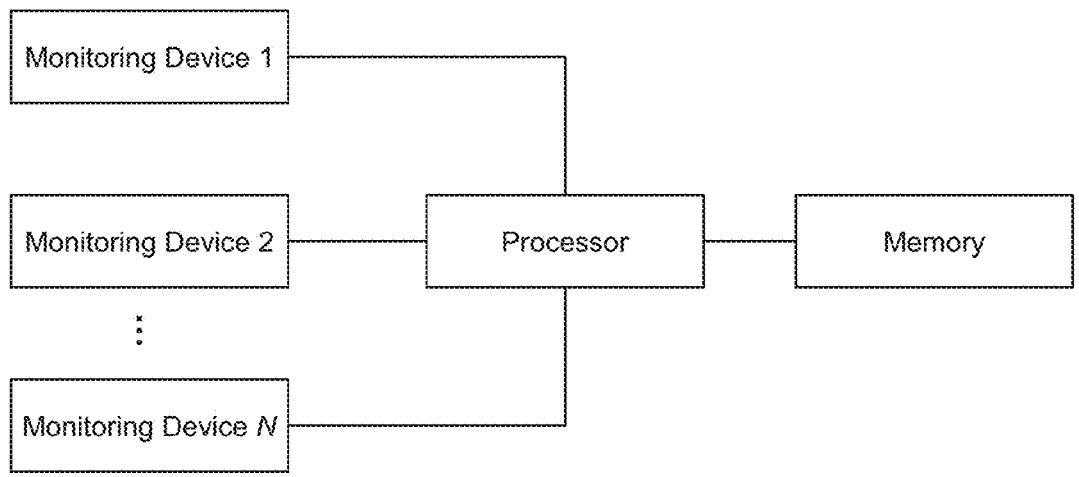
FIG. 1A shows a non-limiting system schematic of the present invention.

Referring to FIG. 1A, in some embodiments, the present invention provides a system configured to monitor spreading depolarization (SD) and repolarization (RP) in a brain during a cardiac event. The cardiac event may be cardiac arrest in which the brain experiences cardiac arrest-induced brain ischemia during the cardiac event. Preferably, the system may be used to gauge severity and prognosticate outcome of a neurological condition of the brain based on the cortical SD and RP.

According to one embodiment, a system for monitoring and determining neurological outcome of a brain post cardiac arrest (CA) may comprise one or more monitoring devices for detecting spreading depolarization (SD) and repolarization (RP) in the brain, a processor operatively coupled to the one or more monitoring devices, and a memory coupled to the processor. The memory, a non-transient storage device, stores one or more metrics for determining a neurological outcome score, and computer-readable instructions that, when executed by the processor, causes the processor to perform operations. These operations include receiving data on SD and RP from the one or more monitoring devices, comparing the SD and RP data to the one or more metrics to determine an estimated neurological outcome score, and identifying a neurological condition of the brain based on the neurological outcome score. Without wishing to be bound to a particular theory or mechanism, SD and RP are biomarkers for neurological outcome post-cardiac arrest and resuscitation, and the neurological outcome score may be used to gauge severity and prognosticate outcome of the neurological condition of the brain in real-time.

In some embodiments, the one or more monitoring devices is an electrophysiological monitoring device for detecting SD and RP in the brain, an optical measurement device for measuring one or more of cerebral blood flow (CBF), tissue oxygenation, and tissue scattering in the brain, or a combination thereof. The optical measurement device may also detect SD and RP. In some embodiments, the memory further comprises computer-readable instructions that, when executed by the processor, causes the processor to perform operations comprising receiving measurements of one or more of CBF, tissue oxygenation, and tissue scattering from one or more optical measurement devices, determining one or more of cerebral metabolic rate of oxygen (CMRO2) from the measurements of CBF and tissue oxygenation, and scattering change onset, duration, and magnitude from the tissue scattering measurements, and comparing one or more of the CMRO2, scattering change onset, duration of scattering change, magnitude of scattering change, CBF, and tissue oxygenation measurements to one or more metrics to determine the estimated neurological outcome score.

According to some embodiments, the one or more metrics may based on measures of neurological status or outcome including, but not limited to, a Glasgow Coma Scale (GCS), Cerebral Performance Category (CPC), a Modified Rankin Scale (mRS), or specific features of a neurological exam.

In some embodiments, the electrophysiological monitoring techniques described herein may comprise a plurality of electrodes configured to be attached to a scalp. In preferred embodiments, the devices may be used to capture cortical spreading depolarization for diagnostic monitoring in patients. In combination or alternative to electrophysiological techniques, the system may implement non-electrophysiological techniques. In one embodiment, the system may include one or more optical measurement devices, such as point measurement devices, diffuse optical measurement devices, or optical measurement devices capable of measuring one or more of the CBF, tissue oxygenation, and tissue scattering through intact human skull. The optical measurement device can measure cerebral blood flow (CBF), tissue oxygenation, tissue scattering, and/or cerebral metabolic rate of oxygen (CMRO2), as well as detecting SD and RP. In one embodiment, the system may comprise an electroencephalogram (EEG) apparatus operatively coupled to an optical measurement device. In some embodiments, the devices may be invasive or non-invasive.

In one embodiment, the system of the present invention can detect SD and RP using EEG/ECoG, and tissue scattering using an optical device. SD and RP may also be detected from CBF, tissue oxygenation, tissue scattering, and/or CMRO2 data obtained by the optical device. The system may be used to monitor a patient with all these parameters during SD and RP to detect SD and RP, which can allow for an assessment/prognosis to be made. Intervening treatments may be administered while continuing to monitor these parameters and thus getting constant feedback to change the interventions. The interventions can include medical treatments for the brain (stimulation and induction of SD and RP), manipulating CBF or CMRO2 in various ways, manipulating the heart (including blood pressure), or other treatments geared towards optimization of the brain.

In other embodiments, the invention features a means or device that can induce SD in a brain during or after a cardiac event, such as cardiac arrest in which the brain may experience cardiac arrest-induced brain ischemia. In yet other embodiments, the invention may include a means or device configured to induce RP of the brain. The means or devices may be chemical stimulation, physical stimulation, electrical stimulation, magnetic stimulation, optical stimulation, soundwave-induced stimulation, or a combination thereof. For example, neurostimulation of the brain may induce SD by causing electric current to flow to a targeted region of the brain. A non-limiting example of neurostimulation is transcranial magnetic stimulation, a non-invasive procedure in which a changing magnetic field is used to cause the flow of electric current via electromagnetic induction. A magnetic field generator is placed on the scalp and operatively coupled to a pulse generator that delivers a changing electric current to the magnetic field generator.

In further embodiments, the invention may also provide a system for monitoring a brain during cardiac arrest-induced brain ischemia. The system may comprise a brain monitoring device, such as the devices described herein or other devices geared to detect SD and RP phenomena. The brain monitoring device can capture SD and RP in the brain.

In some preferred embodiments, the systems described herein can have various configurations for different settings of usage. For example, in an emergency, unexpected cardiac arrest, the system may be portable and easy to use to allow emergency medical personnel, or even a lay person, in or outside a hospital to apply the device quickly. As another example, for the inpatient setting (e.g. intensive care unit, operating room, emergency room, etc.), the system does not necessarily need to be compact or simplified since trained personnel are available and have the time to apply the device for surveillance purposes rather than unexpected emergency situations.

Figure 1B:
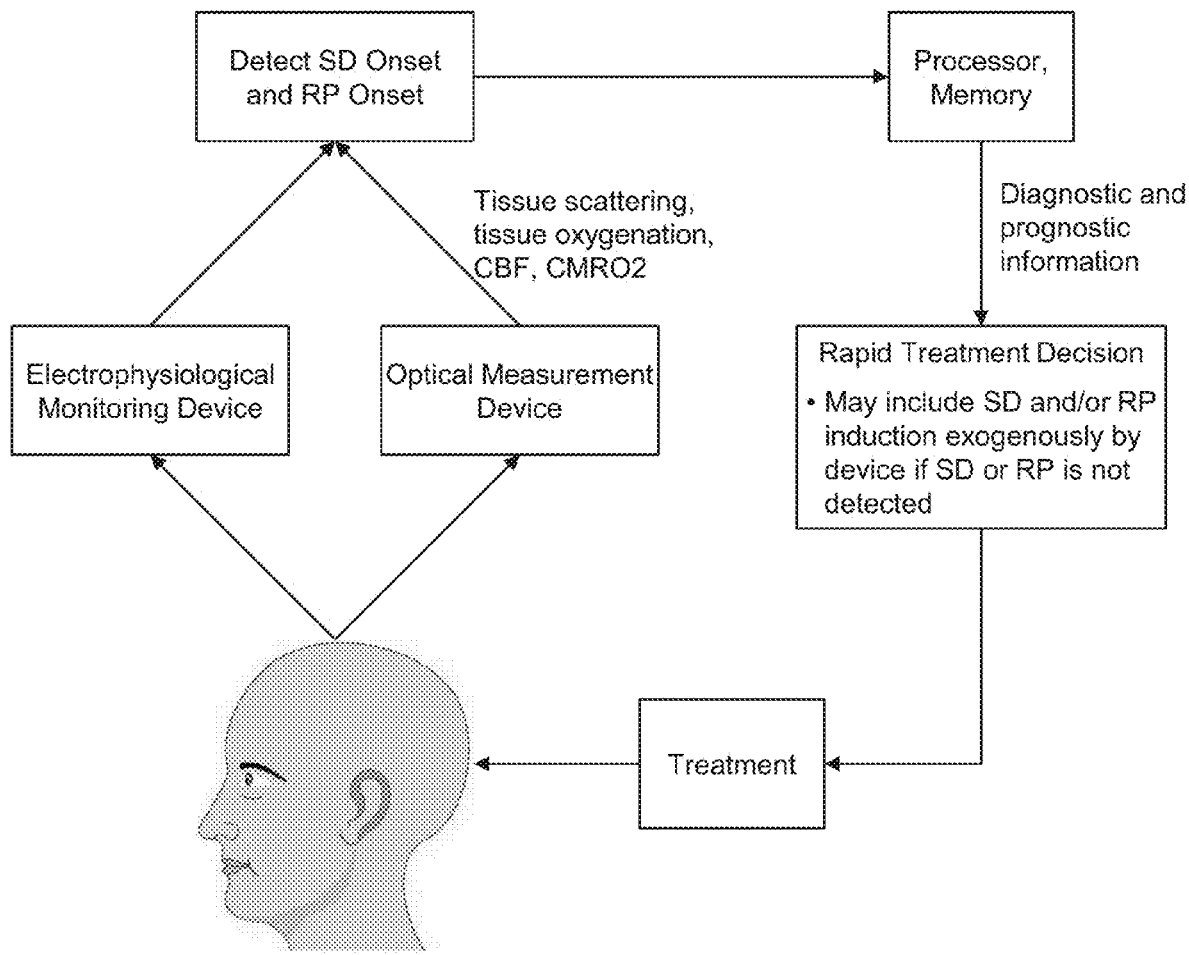
FIG. 1B is a flow chart of a non-limiting procedure of the present invention.

Referring to FIG. 1B, in other embodiments, the present invention provides a method of prognosticating neurological outcome in a subject experiencing cardiac arrest. The method may comprise monitoring the subject's brain for cortical spreading depolarization and monitoring the subject's brain for repolarization after resuscitation. Preferably, prognostication of the neurological outcome may be achieved in real-time. Without wishing to limit the present invention, if SD is detected earlier during cardiac arrest, and/or the repolarization is detected earlier immediately after return of spontaneous circulation, neurological outcome may be better if the subject is successfully resuscitated. As such, SD and repolarization can acts as biomarkers for post-cardiac arrest and resuscitation outcome, respectively.

According to one embodiment, the present invention may also feature a method of improving neurological outcome in a subject during cardiac arrest. The method may comprise detecting spreading depolarization, or a lack or delay thereof, in a brain of the subject post cardiac arrest, resuscitating the subject, detecting repolarization, or a lack or delay thereof, in the brain of the subject post resuscitation, comparing SD and RP data to one or more metrics to determine an estimated neurological outcome score, identifying a neurological condition of the brain based on the neurological outcome score, and administering a treatment to the subject to improve the neurological condition of the brain. The neurological outcome score acts as a gauge of severity and prognosticates outcome of the neurological condition of the brain in real-time. Non-limiting examples treatments that may be administered include therapeutically administering a drug, electrical stimulation, magnetic stimulation, optical stimulation, soundwave-induced stimulation, or a combination thereof.

In other embodiments, the method of improving neurological outcome may further comprise measuring one or more of cerebral blood flow (CBF), tissue oxygenation, and tissue scattering in the brain, determining one or more of cerebral metabolic rate of oxygen (CMRO2) from the measurements of CBF and tissue oxygenation, and scattering change onset, duration, and magnitude from the tissue scattering measurements, and comparing one or more of the CMRO2, scattering change onset, duration of scattering change, magnitude of scattering change, CBF, and tissue oxygenation measurements to one or more metrics to determine the estimated neurological outcome score.

In some embodiments, SD may not be detected, e.g. SD may not occur or it may be delayed after a specific period of time. If SD is not detected or if it is expected to be delayed, SD can be induced earlier to improve neurological outcome. In other embodiments, RP may not have occurred or it may be delayed after a period of time. If RP is not detected or if it is expected to be delayed, RP can be induced earlier to improve neurological outcome. Thus, a lack or delay of SD or RP may indicate that SD or RP should be induced in the patient. In one embodiment, a method of improving neurological recovery in a subject experiencing cardiac arrest may comprise inducing SD in a brain of said subject during or immediately after cardiac arrest. SD may be induced by stimulating the brain, for example, with chemical stimulation, physical stimulation, electrical stimulation, magnetic stimulation, optical stimulation, soundwave-induced stimulation, or a combination thereof. In other embodiments, the method may further comprise inducing early RP of the brain after cardiac arrest. For example, resuscitating the subject after cardiac arrest can induce early RP of the brain and support measures for early induction of RP. In some embodiments, treatments for improving neurological outcome are based on inducing SD and/or RP promptly. On the other hand, if SD and/or RP is already detected, then SD and/or RP may not need to be induced, e.g. detection is only for prognosing.

According to other embodiments, the invention may include a method for improving neurological outcome in a subject during a cardiac event. The method may comprise detecting cortical spreading depolarization in a brain of said subject during the cardiac event to determine a neurological condition of the brain, and administering a treatment to the subject for treating the neurological condition. The treatment may comprise therapeutically administering a drug, chemical stimulation, electrical stimulation, magnetic stimulation, optical stimulation, soundwave-induced stimulation, or a combination thereof. In other embodiments, the method may further comprise monitoring the subject's brain for repolarization. Repolarization may be detected after resuscitation of the subject.

In some other embodiments, the present invention features a method of determining neurological outcome in a subject after cardiac arrest. The method may comprise detecting SD, or a lack or delay of SD, in a brain of the subject post cardiac arrest, detecting RP, or a lack or delay of RP, in the brain of the subject post resuscitation, comparing SD and RP data to one or more metrics to determine an estimated neurological outcome score, and identifying a neurological condition of the brain based on the neurological outcome score. SD and RP are believed to be biomarkers of neurological outcome post-cardiac arrest and resuscitation, respectively. Furthermore, the neurological outcome score can gauge severity and prognosticate outcome of the neurological condition of the brain in real-time. In some embodiments, the method may further comprise measuring one or more of cerebral blood flow (CBF), tissue oxygenation, and tissue scattering in the brain, determining one or more of cerebral metabolic rate of oxygen (CMRO2) from the measurements of CBF and tissue oxygenation, and scattering change onset, duration, and magnitude from the tissue scattering measurements, and comparing one or more of the CMRO2, scattering change onset, duration of scattering change, magnitude of scattering change, CBF, and tissue oxygenation measurements to one or more metrics to determine the estimated neurological outcome score. In other embodiments, the method also includes inducing SD in the brain during or immediately after cardiac arrest and/or inducing RP in the brain during or immediately after resuscitation. If SD is not detected or if it is expected to be delayed after a specific period of time, prognosing poor outcome, SD can be induced earlier to improve neurological outcome. In other embodiments, RP may not be detected. If RP is not detected or if it is expected to be delayed after a period of time, prognosing poor outcome, RP can be induced earlier to improve neurological outcome.

As will be described in the following example, a preclinical model mimicking an intensive care unit along with a multimodal monitoring setup including optical imaging and electrophysiology was used to characterize SD in the brain during CA, RP in the brain following resuscitation, and the relationship between SD/RP parameters and neurological recovery. The present invention demonstrates, for the first time, that earlier SD onset correlates with, and is predictive of, improved neurological outcome (24-hr NDS). Including RP onset into this model provides an additional improvement over using SD alone. Lower values of optically-measured parameters related to CBF, metabolism, flow/metabolism coupling, and cytotoxic edema during SD and RP were correlated with improved neurological recovery. Characterizing SD and RP in this manner demonstrated strong potential to provide (1) ultra-early prognostication of neurological recovery from global ischemia and (2) elucidation of potentially modifiable mechanisms of cerebral response to global ischemia and reperfusion. These metrics may be used to inform clinically translatable interventions for CA patients during CA itself or immediately post-resuscitation, enabling patient-specific treatment at early time points that may be critical for optimizing neurological recovery. These findings may also be translatable to other ischemic or non-ischemic conditions, such as focal stroke, subarachnoid hemorrhage, traumatic brain injury, traumatic exsanguination leading to ischemic brain injury, or other situations leading to acute brain injury.

EXAMPLE

The following is a non-limiting example of practicing the present invention. It is to be understood that said example is for illustrative purposes only, and is not intended to limit the invention in any way. Equivalents or substitutes are within the scope of the invention.

The most common type of cardiac arrest in the in-hospital setting is non-shockable cardiac arrest. Since patients in the hospital setting are closely monitored, including hemodynamic monitoring and brain monitoring, the inventors focused on electrophysiological monitoring of the brain (i.e. electroencephalography; EEG). To model patients in the hospital, this study was undertaken in an animal research laboratory, where the brain can be monitored and controlled cardiac arrest and resuscitation can be induced while evaluating outcome. In this experiment, the inventors investigated the relationship between the timing of SD dynamics during CA and neurological outcome 90 min and 24 hrs after CA+CPR.

Preclinical Model

Figure 1C:
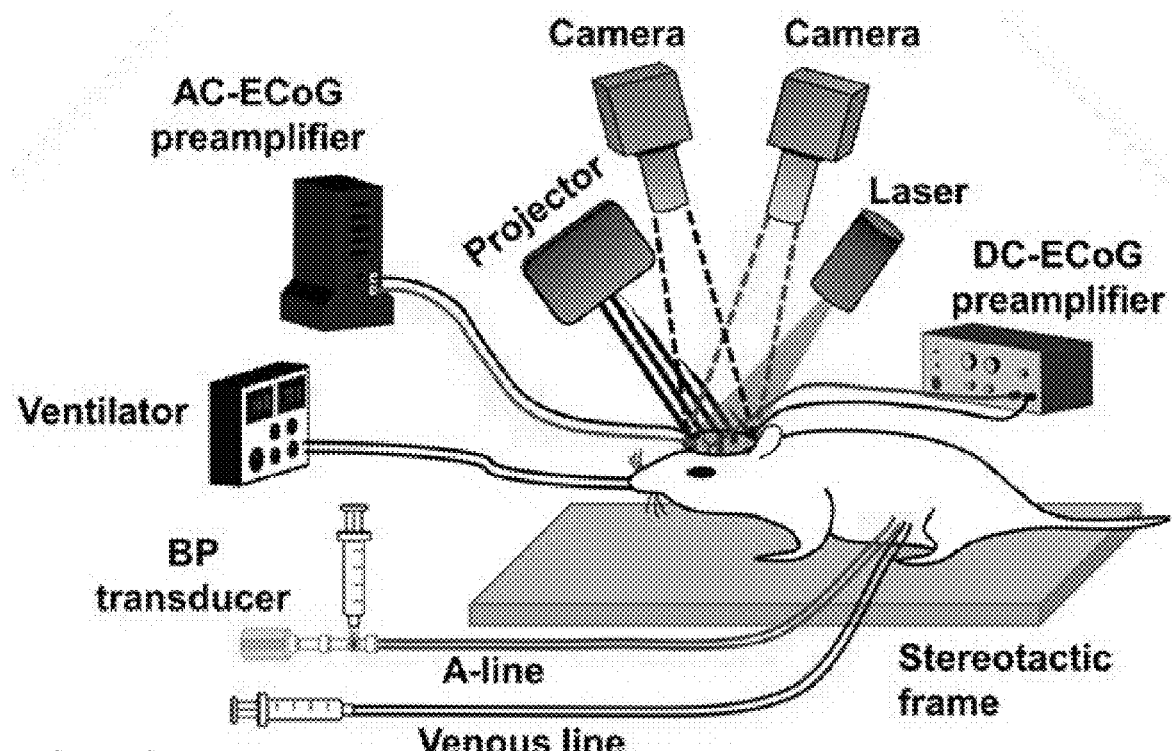
FIG. 1C shows a non-limiting embodiment of an animal model of ACA and CPR for Cohort 3, measured with multimodal monitoring platform. This platform includes arterial-line blood pressure (BP), AC-ECoG, laser speckle imaging (LSI) for measuring cerebral blood flow (CBF), and spatial frequency domain imaging (SFDI) for assessing tissue oxygenation (StO2) and scattering. The combination of LSI and SFDI enables measurement of cerebral metabolic rate of oxygen (CMRO2).
Figure 1D:
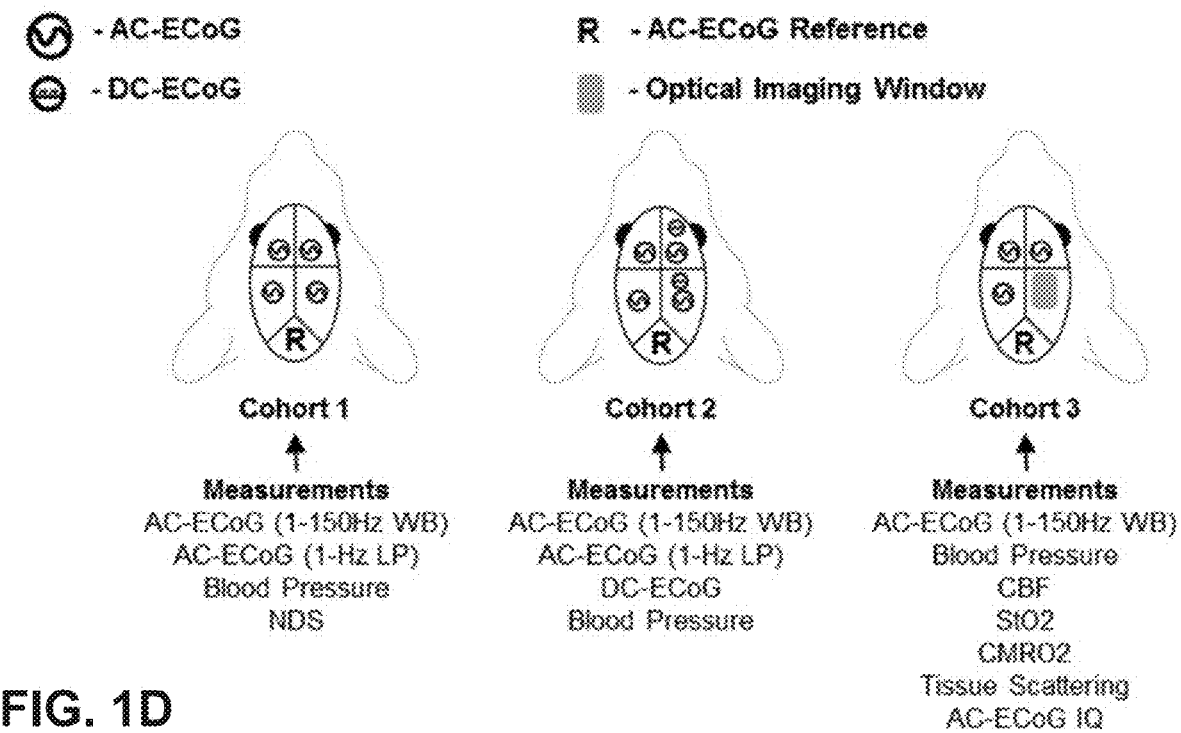
FIG. 1D is a list of measurement modalities, along with schematics of electrode placement for AC-ECoG and direct current (DC) ECoG, for three cohorts.

Referring to FIGS. 1C-1D, male Wistar rats were intubated and received femoral artery and vein cannulation to enable arterial blood pressure (BP) monitoring and drug delivery, respectively. During the ACA experiment as shown in FIG. 1E, isoflurane was washed out over a 3 min period and a paralytic agent (vecuronium) was given. Following the washout period, CA was induced by turning off the ventilator for 5, 7, or 8 min, depending on experimental cohort. Subsequently, CPR was initiated by turning the ventilator back on, giving epinephrine and sodium bicarbonate, and performing manual chest compressions. Chest compressions were continued until return of spontaneous circulation (ROSC), after which the rats were monitored continuously for an additional 2-4 hours.

Three separate cohorts of rats, each with different multimodal monitoring techniques, were used (FIG. 1D). In Cohort 1, surgery to implant screw electrodes for AC-ECoG recordings was done 1 week prior to the CA experiment. All rats underwent an 8 min ACA and received neurological testing (Neurological Deficit Score; NDS) at 24 hrs post-ROSC (FIG. 1F). Rats in Cohort 2 also underwent 8 min ACA, and had two additional ECoG silver chloride (Ag/AgCl) electrodes implanted to record DC potential. The Ag/AgCl electrodes were made by chloridizing silver wires (Stoelting 50880) in household bleach. The Ag/AgCl electrodes were implanted 1 mm into the cortex in the right hemisphere, within 3 mm of the right occipital AC-ECoG screw electrodes.

Referring to FIG. 1C, Cohort 3 was studied with optical imaging after performing a partial craniectomy over the right parietal lobe on the day of the experiment. Rats in this cohort were monitored continuously with three AC-ECoG electrodes, but did not have DC-ECoG monitoring. In addition, these animals were split into a "mild CA" (5 min asphyxia) and a "moderate CA" (7 min asphyxia) group to mimic the variability of CA durations encountered in an intensive care setting. Rats in this cohort were monitored for 2 hrs post-ROSC and then sacrificed, as the presence of the craniectomy prevented them from being survived. 24-hr NDS was unable to be performed on Cohort 3, so 90 min post-ROSC ECoG information quantity (IQ) was used to measure short-term neurological outcome following resuscitation.

Data Acquisition and Post-Processing

Post-processing of arterial BP, AC- and DC-ECoG, and optical imaging data was performed using MATLAB.

Arterial BP and Arterial Blood Gas (ABG)

For all cohorts, BP was measured continuously at 191 Hz from an arterial line. Mean arterial pressure (MAP) was determined at 1-Hz. ABGs were acquired prior to start of experiment with i-STAT 1 Analyzer.

AC/DC-EcoG

For all cohorts, AC-ECoG data was acquired at 1526 Hz with the TDT RZ5D BioAmp Processor and PZ2 preamplifier with inbuilt 0.35 Hz-7.5 kHz band-pass filter. In Cohort 2, in parallel with AC-ECoG data, DC-ECoG data was acquired at 305 Hz with Duo 773 and Model 750 electrometers.

For wide-band (WB) ECoG, AC-ECoG data was 60-Hz notch filtered and 1-150 Hz band-pass filtered. To visualize SD on AC-ECoG, a 1-Hz LP filter was applied. A 1-Hz LP filter was also applied to DC-ECoG data to remove noise.

For Cohort 3, the median ECoG IQ from 90 to 100 min post-ROSC was calculated from WB ECoG. The baseline microstates were determined from the final minute of anesthesia washout prior to start of asphyxia. AC-ECoG IQ was also normalized to this baseline period.

Optical Imaging

Rats in Cohort 3 underwent continuous laser speckle imaging (LSI) and multispectral spatial frequency domain imaging (SFDI) throughout the experiment. Both LSI and SFDI utilize diffuse near-infrared light to interrogate subsurface tissue structure and function. LSI is a technique to measure blood flow in preclinical models and humans. SFDI is a technique that enables separate quantification of the diffuse optical absorption and scattering coefficients of tissue. The absorption coefficient, when measured at multiple near-infrared wavelengths, provides information regarding concentrations of oxygenated and deoxygenated hemoglobin ($ctHbO_2$, ctHb, respectively) in tissue. The scattering coefficient provides information about structure, distribution, and concentration of tissue components, such as cell membranes, nuclei, and mitochondria. Increased tissue scattering is an indicator of cytotoxic edema that accompanies SD. Combining cerebral blood flow (CBF) data from LSI with tissue oxygenation data from SFDI enables calculation of cerebral metabolic rate of oxygen consumption ($CMRO_2$).

Data Analysis

Exclusion Criteria

For Cohort 1, three rats were excluded from analysis due to poor quality AC-ECoG recordings. SD was observed in n=27 rats. RP onset was unable to be determined in 5 rats, so n=22 for analysis involving RP onset. No rats were excluded from Cohort 2 (n=5). For Cohort 3, one rat was excluded due to prolonged CPR and blood loss complications. Thus, for LSI data n=10 (5-min ACA=5, 7-min ACA=5). One additional rat was excluded from SFDI analysis due to an instrument malfunction. Thus, for SFDI data n=9 (5-min ACA=4; 7-min ACA=5).

LSI Data: Speed and Spatial Propagation of Spreading Ischemia

To characterize the CBF waves, videos of CBF images were created. Each frame of the video had CBF images averaged over one-second intervals. The videos were used to characterize the periods of spreading CBF waves. The spatial onset and completion locations of each wave and their corresponding times were extracted after visual inspection of each video. To calculate the speed of the wave, the distance between the onset and completion locations and the duration of the waves were used. To quantify the total amount of brain perfusion prior to the onset of spreading ischemia, the relative CBF (rCBF) time-course signal was integrated over time from the onset of asphyxia to the onset of spreading ischemia. rCBF was normalized to the mean CBF calculated over the one-minute interval immediately prior to the onset of asphyxia.

LSI Data: Vessel Diameter

Custom-written MATLAB code was used to compute vessel diameter using one second-averaged CBF images. First, the centerline for a given vessel of interest was defined, followed by the bounds for a line that was perpendicular to the centerline. For each time point, the CBF values from the perpendicular line were extracted, and a Gaussian was fitted through the CBF values. If the R-squared of the Gaussian fit was greater than 0.9, the full-width half-maximum (FWHM) was computed from the Gaussian fit. If the value was less than 0.9, the diameter was assigned a not-a-number value. This process was repeated on 5 to 10 vessels per experiment.

SFDI Data: Tissue Scattering and Oxygenation

Custom-written MATLAB code developed at Beckman Laser Institute was used to fit a photon propagation model (Monte Carlo simulation) to the data to extract maps of the tissue absorption and scattering coefficients at the three measured wavelengths (655 nm, 730 nm, 850 nm). The absorption coefficient was then fit to a linear combination of oxygenated and deoxygenated hemoglobin absorption to extract the concentrations of oxy- and deoxy-hemoglobin (ctHbO2, ctHb) and the tissue oxygenation (StO2). To generate ctHbO2, ctHb, StO2, and tissue scattering time-courses, a region of interest (ROI) over the parenchyma (i.e., not atop a major vessel) was selected for each individual rat. Each rat's ROI was kept constant for every time point in an experiment.

LSI+SFDI Data: CMRO2

To generate CMRO2 time-courses, LSI data was combined with SFDI data. For LSI data, an ROI covering nearly the entire craniectomy was used. For SFDI data, an ROI atop a vein was used when calculating ctHb and ctHbO2. Note that the CMRO2 calculation used a different ROI for the SFDI data than the initial scattering and absorption calculation. This is because the ctHb and ctHbO2 in a venous ROI were considered a better indicator of the oxygen consumed by the brain, an important distinction for the CMRO2 formula.

Multimodal Parameter Set

For each cohort, a multimodal set of parameters was extracted from the data pre- and post-ROSC to analyze several associations. In Cohort 1, these parameters included: (i) time to AC-ECoG SD onset during ACA; (ii) time to AC-ECoG RP onset post-ROSC; (iii) area under curve (AUC) of MAP from start of asphyxia to SD onset; (iv) AUC of MAP from ROSC to RP onset.

In Cohort 3, the parameter set was comprised largely of quantities obtained from the optical measurements. In this cohort, SD and RP onset were most reliably measured via spatial propagation of tissue scattering. The parameters extracted from Cohort 3 included: (i) spreading ischemia and spreading edema onsets during ACA; (ii) RP onset via scattering wave post-ROSC; (iii) percentage change in scattering during SD; (iv) AUC of CBF curve from start of asphyxia to SD onset; (v) AUC of CBF curve/AUC of CMRO2 curve from start of asphyxia to SD onset; (vi) CBF/CMRO2 at SD onset; (vii) AUC of MAP, CBF, and CMRO2 from ROSC to RP onset.

Neurological Outcome Categorization

The high vs. low NDS cutoff for representative rats from Cohort 1 was defined by the median NDS of 49. In Cohort 3, rats with median AC-ECoG IQ>0.75 from 90-100 mins post-ROSC were defined as high IQ, and median AC-ECoG IQ<0.75 at 90-100 mins post-ROSC as low IQ.

Statistical Models and Tests

Statistical testing was performed with R (v.1.1.456) and MATLAB. Unsupervised hierarchical clustering of Pearson (Cohort 1) and Spearman (Cohort 3) correlations were performed for correlation matrices with the ggcorrplot package (v0.1.2) of R. To develop linear regression models for Cohort 1, the leaps package (v3.0), a regression subset selection package, was utilized. For analyses involving Cohort 3, 5- and 7-min ACA rats were combined, as asphyxial duration was not a significant covariate in the analysis. Wilcoxon rank-sum tests were performed for analyses comparing the high and low IQ groups in Cohort 3.

Using linear regression models generated for Cohort 1, receiver operating characteristic (ROC) curves were generated by varying the NDS threshold for good vs poor neurological outcome. Optimal sensitivity and specificity were determined using Youden's J statistic.

Results

Multimodal Detection of Spreading Depolarization (SD) During ACA

Figure 2D:
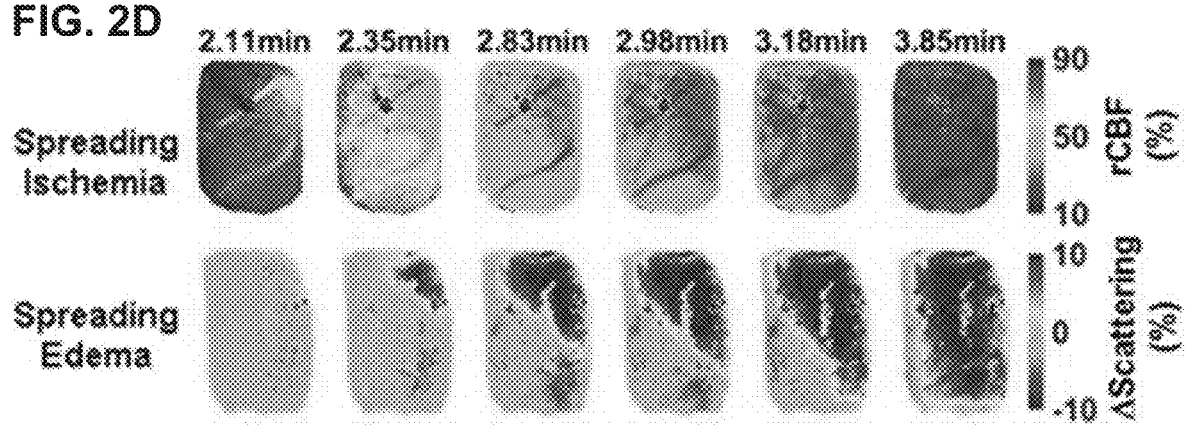
FIG. 2D shows hallmarks of SD measured with optical imaging include spreading ischemia (spatially-propagating CBF wave) and spreading edema (spatially-propagating tissue scattering wave).

In the hypoxic-ischemic model of CA, AC-ECoG silencing, also described as non-spreading depression, was induced within 1 min of the start of asphyxia (FIGS. 2B-2C). SD was detected at approximately 1.9-2.5 min. As shown in FIG. 2A, for Cohort 1, an AC-ECoG marker for SD onset was determined manually by the $2^{nd}$ negative deflection on the 1-Hz LP ECoG during the period of electrocerebral silence. The $2^{nd}$ negative deflection was often prominent and thus utilized to mark SD onset, because the initial deflections associated with SD onset were not readily apparent across different cohorts of rats. AC-ECoG determination of SD onset was verified with DC potential recordings in Cohort 2 (FIG. 2B). In Cohort 3, SD was not visible on AC-ECoG, possibly due to electrical noise introduced by optical instruments, along with prolonged surgeries inducing higher stress. Instead, SD onset for Cohort 3 was marked by the onset of the scattering wave (FIG. 2D), indicative of cytotoxic edema. SD also coincided with a steady increase in tissue oxygenation (StO2) (FIG. 2C).

Spatiotemporal SD-Related Features During ACA

Figure 2E:
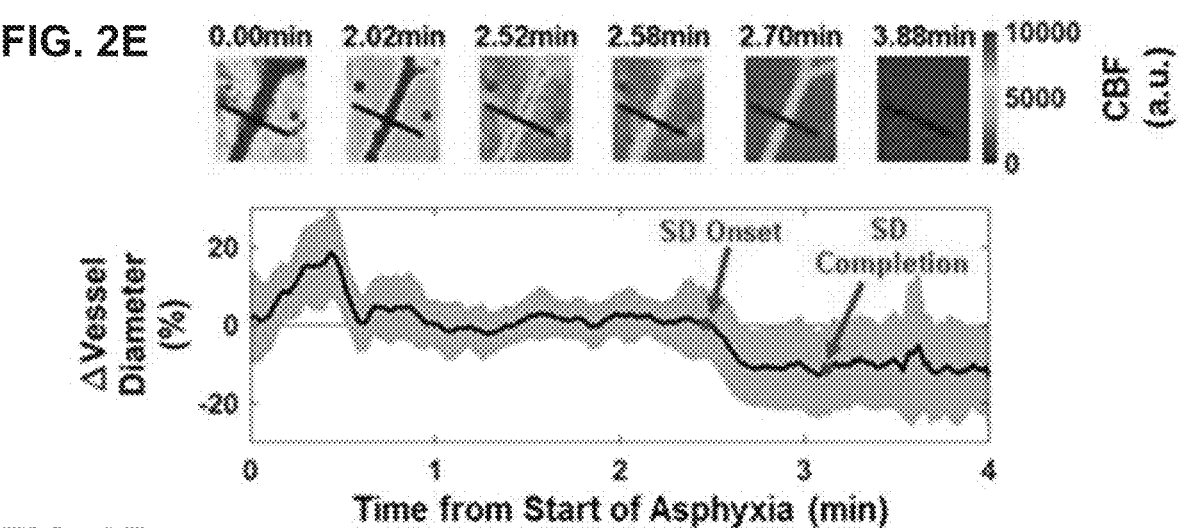
FIG. 2E shows measurements of vasoconstriction during the spreading waves, confirming SD.
Figure 2F:
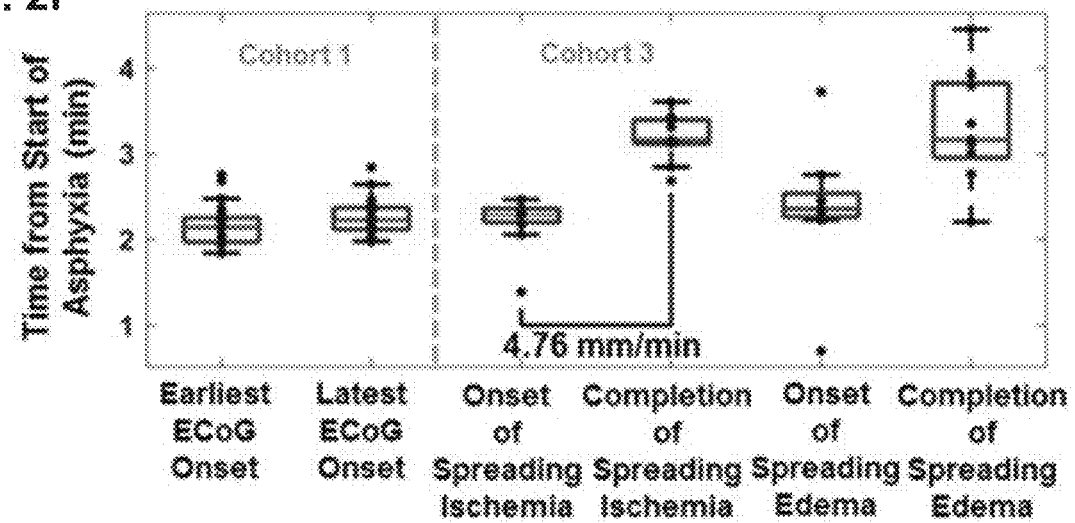
FIG. 2F shows multifocal SD onsets with earliest and latest SD onsets across the 4 AC-ECoG channels in Cohort 1 separated by 7.2±7 sec. The speed of spreading ischemia was 4.76 35 1.10 mm/min.

In Cohort 3, spreading ischemia was observed to travel from lateral to medial within the craniectomy (FIGS. 2D-2F). FIGS. 2E-2F show the detected vasoconstriction and measured speed of spreading ischemia (~4.75 mm/min), respectively. SD onset did not always occur simultaneously across the cortex in Cohort 1 (FIG. 2F). The largest observed range of onset times across the 4 channels was 28 sec.

Earlier Depolarization and Smaller Increases in Scattering are Associated with Better Neurological Outcome Earlier SD onset in Cohort 1 was associated with better neurological outcome (FIGS. 3A-3B). The earliest onset among the 4 channels provided the strongest correlation with NDS ($r=-0.8$), with mean ($r=-0.78$) and latest ($r=-0.72$) channel onsets providing progressively weaker correlations. Earliest SD onset was used for further analysis. In Cohort 3, earlier SD onset trended towards higher AC-ECoG IQ. Notably, a smaller increase in tissue scattering during SD was associated with higher AC-ECoG IQ post-ROSC (FIGS. 3C-3E).

Algorithmic Determination of AC-ECoG SD Onset

Figure 3H:
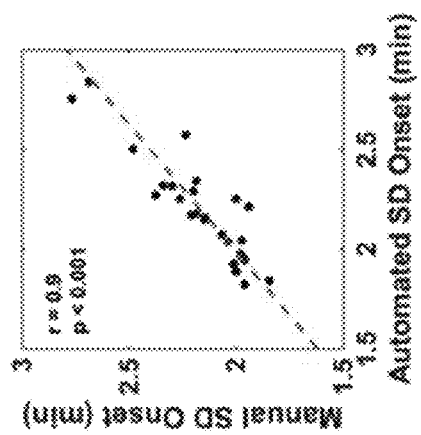
FIG. 3H shows that the earliest manual and automated SD onsets correlate strongly (r=0.9).
Figure 3I:
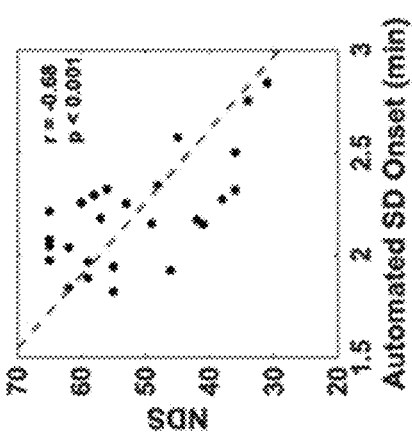
FIG. 3I shows that automated SD onset correlates with NDS with r=−0.68, while manual SD onset correlates with NDS with r=−0.8.
Figure 3G:
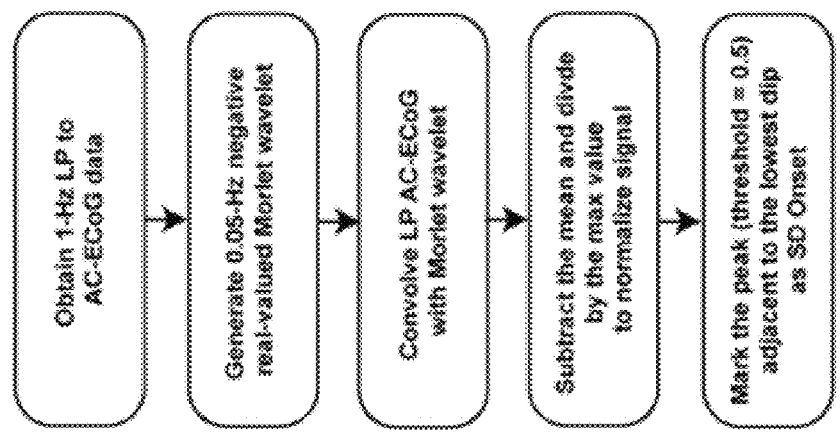
FIG. 3G is an algorithm methodology involving convolution and thresholding for $2^{nd}$ negative deflection detection.
Figure 3F:
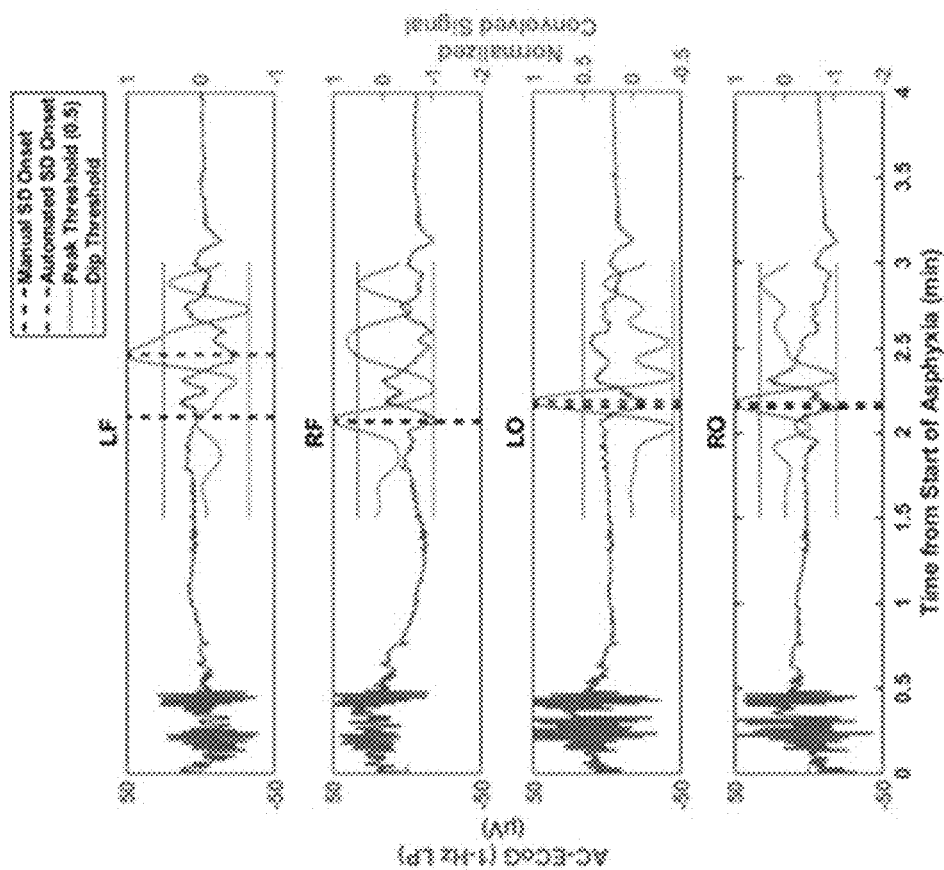
FIG. 3F shows an automated algorithm detection of AC-ECoG SD onset.

To verify manual detection of SD onset for Cohort 1, an automated algorithm was developed to similarly determine the 2nd negative deflection for SD onset (FIG. 3G). As shown in FIGS. 3H-3I, the automated SD onsets confirmed the manual onsets ($r=0.9$) and the association between SD onset and NDS ($r=-0.68$, $p<0.001$).

Figure 4A:
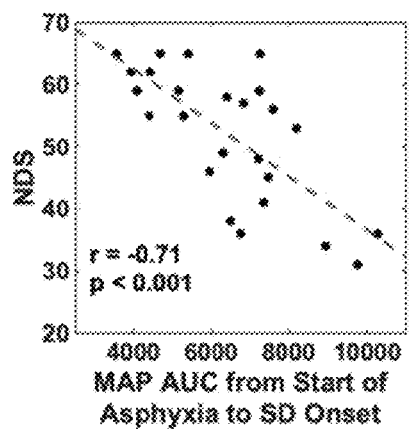
FIGS. 4A-4H shows various graphs demonstration greater perfusion and higher cerebral perfusion-metabolism ratio up to SD onset correlate with worse outcome.
Figure 4B:
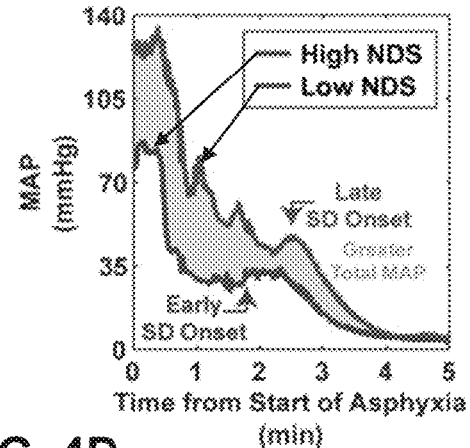
Figure 4C:
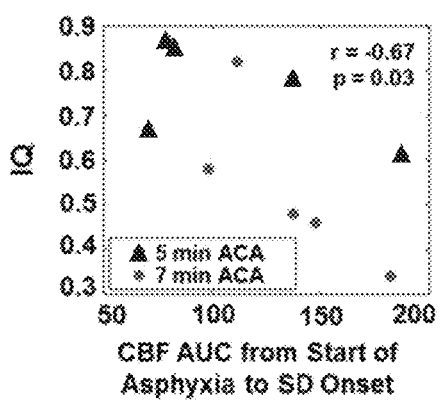
Figure 4D:
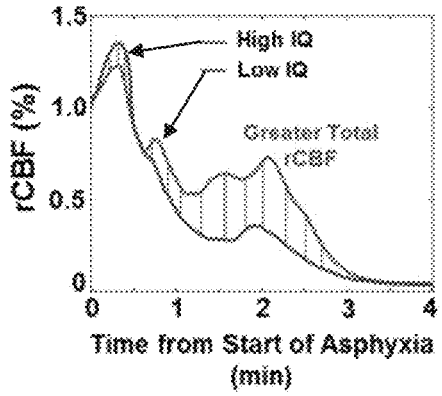
Figure 4E:
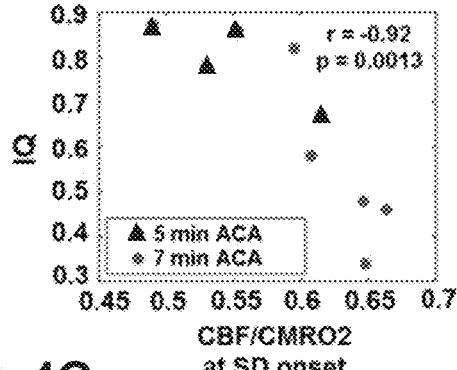
Figure 4F:
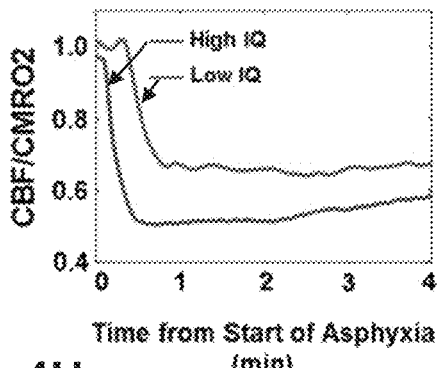
Figure 4G:
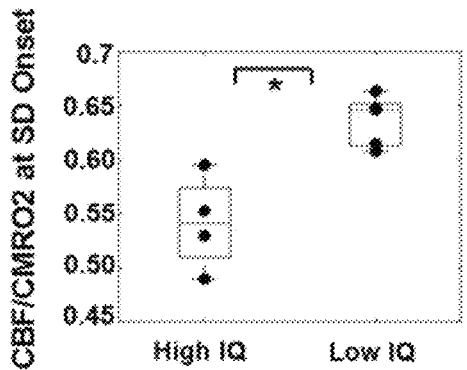
Figure 4H:
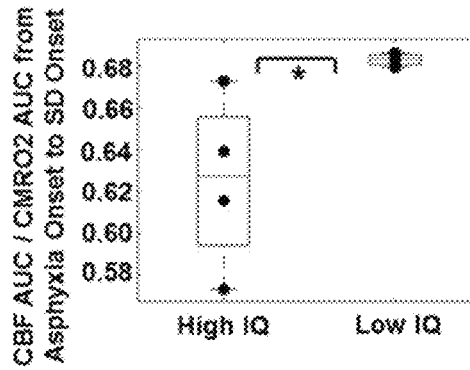

Greater Global Perfusion, Cerebral Perfusion, and Higher CBF/Metabolism Ratio Until SD Onset is Associated with Worse Neurological Outcome Higher total peripheral blood pressure (MAP) and CBF, from start of asphyxia to SD onset, were associated with worse neurological outcome (FIG. 4A). In Cohort 1, higher average blood flow (i.e., mean MAP) was also associated with lower NDS. Additionally, in Cohort 3, low IQ rats had higher CBF (FIGS. 4C-4D) and higher flow-metabolism ratio (FIGS. 4E-4H), suggesting excess cerebral perfusion during ACA.

Multimodal Detection of Repolarization Following Resuscitation

Figures 5A, 5B, 5C:
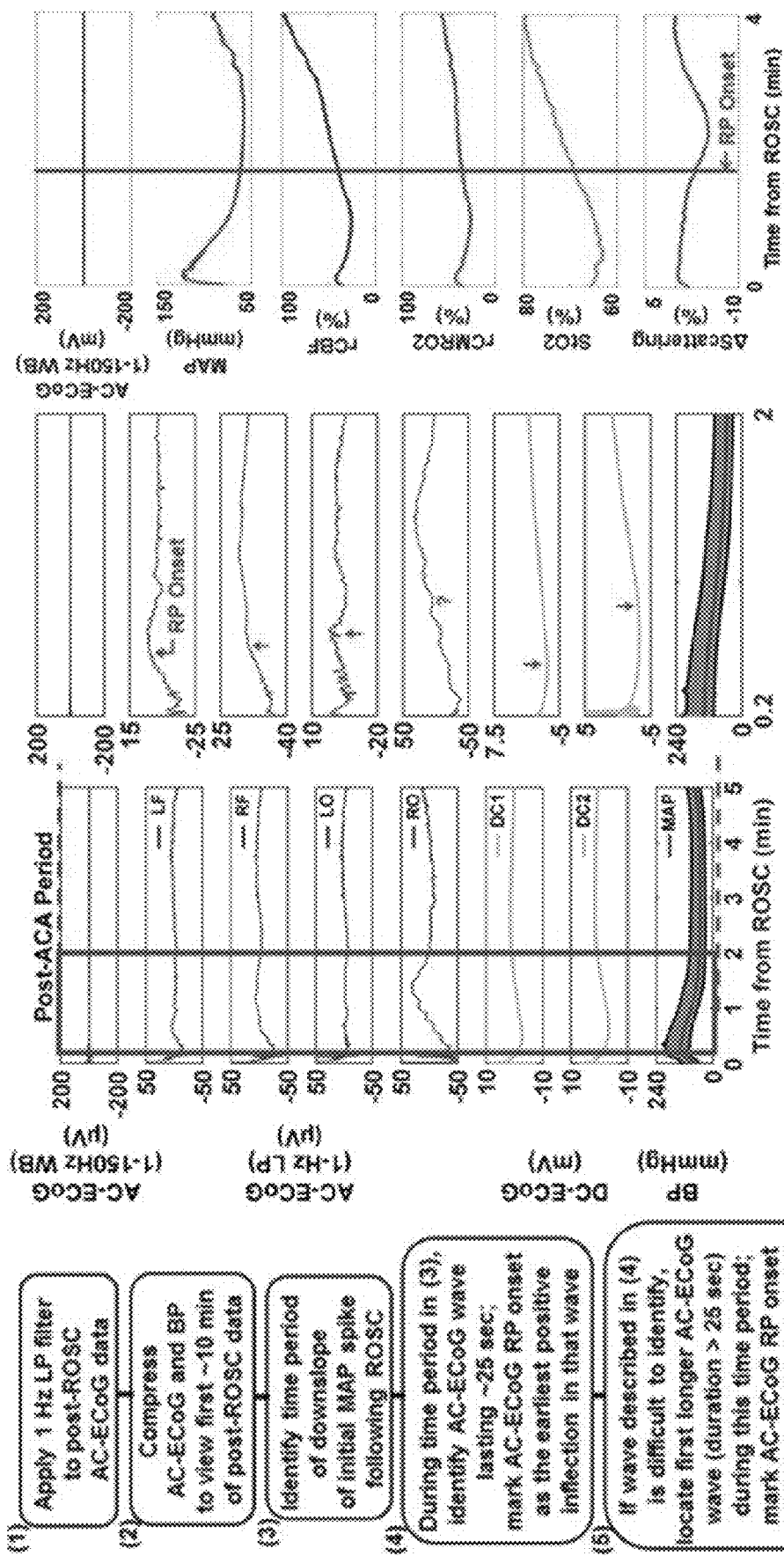
FIG. 5A is a flow diagram for detecting repolarization (RP) following ROSC with multiple measurement modalities.
FIG. 5B show post-ROSC RP not visible in 1-150 Hz WB AC-ECoG, but large waves are visible in 1-Hz LP AC-ECoG. RP onset was discovered to occur during the downslope of the spike in post-ROSC BP. RP onset is marked by a large, slow positive deflection on LP AC-ECoG during the BP downslope, approximately corresponding to an inflection point on the DC potential.
FIG. 5C shows an inflection point in tissue scattering (attributed to neuronal RP) observed during the same time period as the wave in FIG. 5B, even though no such feature is observed in cerebral blood flow (rCBF), cerebral metabolic rate of oxygen (rCMRO2), or tissue oxygenation (StO2). Onset of RP, as defined by onset of spatial propagation of tissue scattering change in optical imaging window, is denoted by the gray vertical line.
Figure 5D:
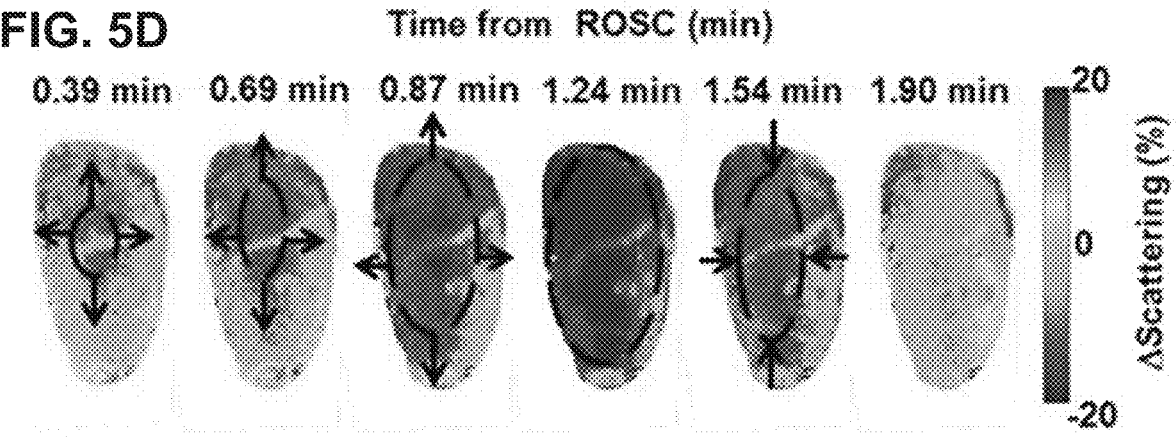
FIG. 5D shows spatiotemporal changes in rat brain scattering coefficient within the first 2 min post-ROSC provide a potential optical biomarker of spreading repolarization.

RP onset was identified on low-pass AC-ECoG by utilizing MAP (FIGS. 5A-5B). In Cohort 2, it was observed that RP on the DC channels, marked by a rise in the DC potential, invariably initiated during the downslope of the initial MAP spike following ROSC. RP onset was marked by a positive deflection in the low-pass AC-ECoG during the initial period of post-ROSC MAP decrease. Due to artifact or inability to determine RP onset, 5 (out of 27) rats of Cohort 1 were excluded from further RP onset analysis. AC-ECoG determination of RP onset was more difficult to determine than SD onset. RP onset for Cohort 3 was determined by visual inspection of the tissue scattering maps, which showed complex spatiotemporal dynamics during this time period (FIG. 5D).

Earlier Repolarization is Associated with Better Neurological Outcome

Figure 5E:
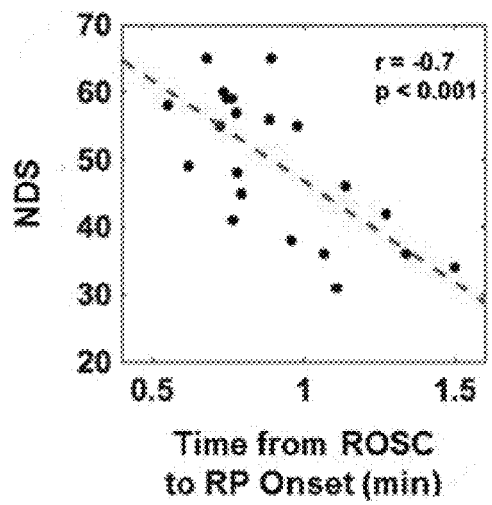
FIGS. 5E-5F show that earlier RP onset in Cohort 1 is associated with better neurological recovery (NDS). Arrows indicate RP onset.
Figure 5F:
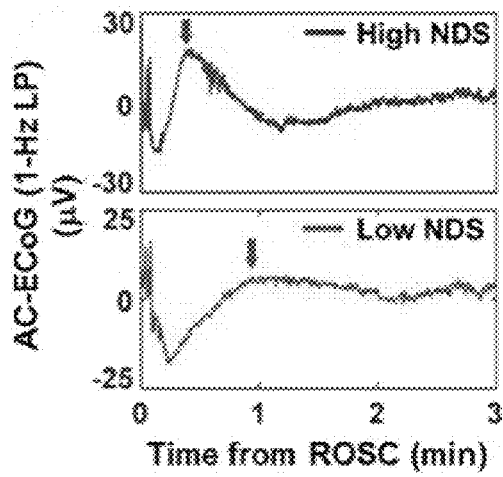

Earlier ECoG RP onset in Cohort 1 was associated with better neurological recovery (FIGS. 5E-5F). Similar to SD onset, the earliest RP onset among the 4 channels exhibited the strongest correlation with NDS so earliest onset was again utilized for further analysis.

Figure 5G:
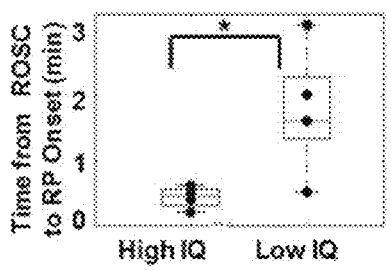
FIGS. 5G-5H show that for Cohort 3, RP onset was determined by start of the scattering wave, and high IQ rats repolarized significantly earlier than low IQ rats.
Figure 5H:
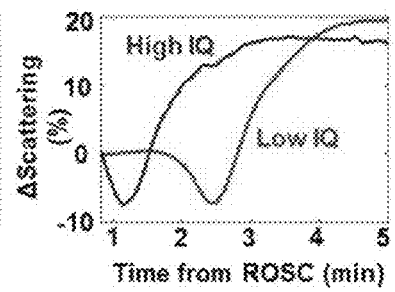
Figure 5I:
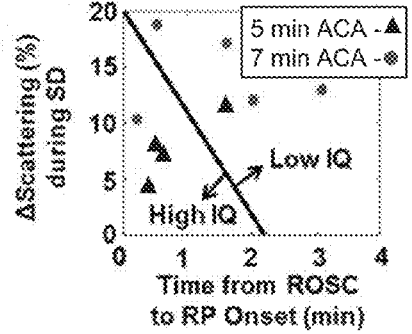
FIG. 5I is a plot of RP onset against the percentage change in scattering during SD. High and low IQ rats formed separate clusters, and rats with smaller scattering increases during SD tended to repolarize earlier. Earlier RP onset is associated with better outcome.
Figure 6A:
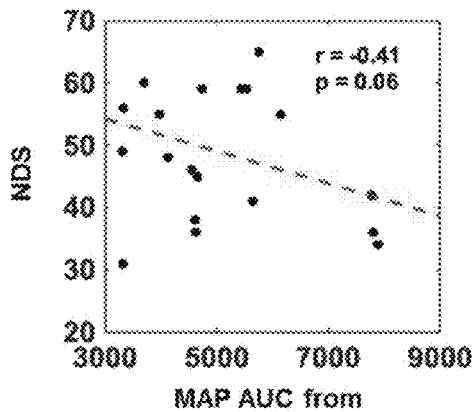
FIGS. 6A-6F are graphs showing greater reperfusion and cerebral metabolism from ROSC to RP onset are associated with worse outcome.
Figure 6B:
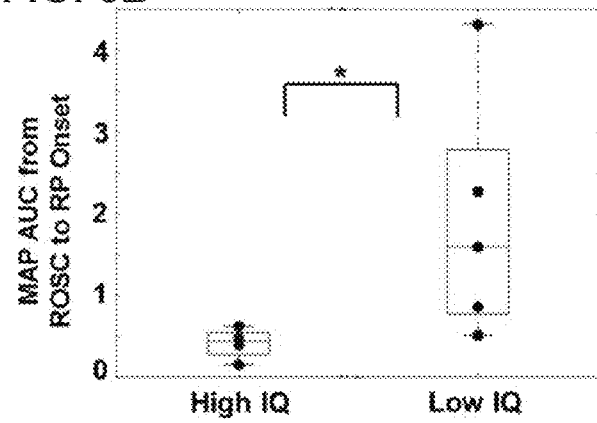
Figure 6C:
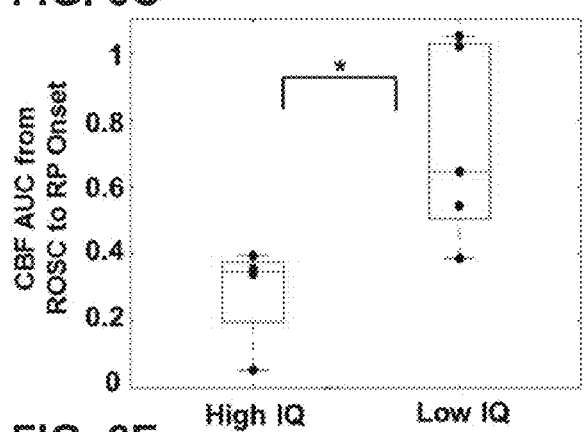
Figure 6D:
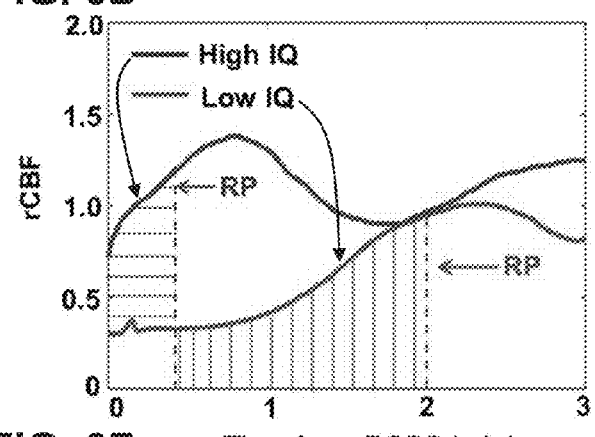
Figure 6E:
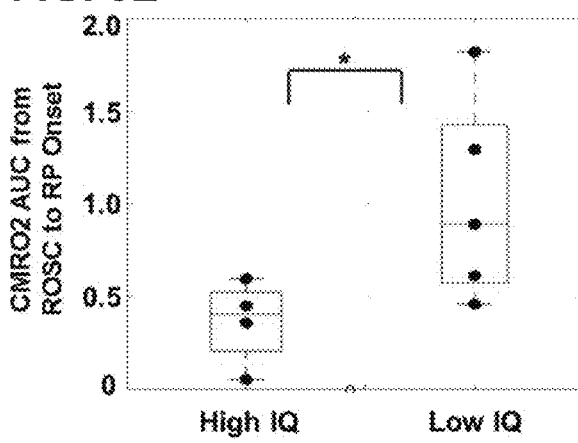
Figure 6F:
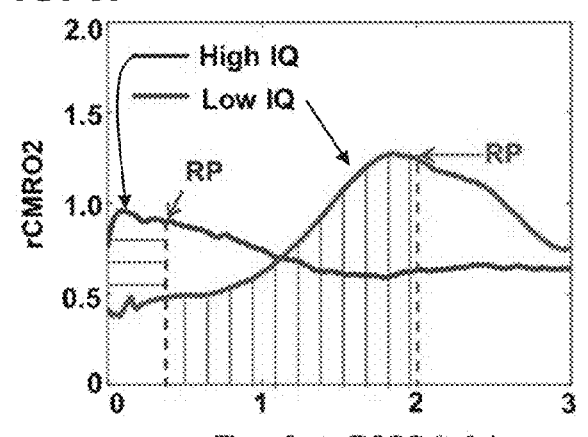

High NDS rats had significantly earlier RP onset than low NDS rats (FIGS. 5E-5F). In Cohort 3, high IQ rats had significantly earlier RP onset times than low IQ rats, as measured with tissue scattering (FIGS. 5G-5H). Interestingly, when RP onset was plotted against change in scattering during SD, high and low IQ rats separated into distinct clusters, with high IQ rats tending to have earlier RP onset and smaller increases in scattering during SD (FIG. 5I).

Total Depolarization Duration from SD Onset to RP Onset is not Associated with Neurological Outcome Since the depolarization period is commonly believed to be injurious, the total combined duration of depolarization pre- and post-CPR was examined. In Cohort 1, the time durations from SD onset until start of CPR and from ROSC until RP onset were added to formulate a combined SD duration for each AC-ECoG channel. There was no association between combined depolarization duration and NDS, likely due to earlier depolarizing rats also repolarizing earlier.

Higher Global Perfusion, Cerebral Perfusion, and Cerebral Metabolism from ROSC to RP Onset are Associated with Worse Neurological Outcome More total peripheral (global) blood flow, CBF, and cerebral metabolism from ROSC to RP onset trended toward worse neurological outcome. Rats in the low IQ group had significantly greater peripheral and cerebral perfusion and metabolism during this period than rats in the high IQ group (FIGS. 6B-6F). Average MAP from ROSC to RP onset was not correlated with NDS, which may indicate that the aforementioned RP relationships are primarily dictated by duration of time between ROSC and RP onset (FIGS. 5E-5G)

SD and RP Onsets Predict Neurological Outcome

Thirteen parameters were tested for inclusion in a linear regression model to predict NDS in Cohort 1. SD onset (FIG. 7A), RP onset (FIGS. 8A and 8C), and baseline glucose (FIGS. 8A and 9C) had the strongest correlations with NDS. Referring to FIGS. 7A-7D, SD onset prediction of NDS was significantly improved by addition of RP onset ($p=0.018$). In FIGS. 8A-8D, RP onset prediction of NDS was significantly improved by addition of baseline glucose ($p=0.037$). Using both SD onset and RP onset in the model provided the most accurate predictions of NDS (FIGS. 7C-7D).

The four models were further utilized to predict high vs. low NDS. SD onset and RP onset alone correctly predicted 18/22 rat outcomes (81.82% accuracy), while SD onset plus RP onset and RP onset plus baseline glucose correctly predicted 20/22 outcomes with 90.91% accuracy.

Discussion

The present invention provides the first demonstration that earlier SD during CA is prognostic of better neurological outcome after resuscitation. The characteristics of SD were verified by measuring a DC potential shift concomitant with the observed AC-ECoG ultra-slow wave. The SD onsets detected with a manual algorithm were confirmed by an automated algorithm ($r=0.9$), which supported the association between SD onset and NDS ($r=-0.68$, $p<0.001$). Additional verification was provided by optically-measuring spreading ischemia (via CBF) and edema (via tissue scattering) with similar onset time as the ultra-slow ECoG wave. Tissue scattering changes were indicative of cytotoxic edema and neuronal injury, and the magnitude of the scattering increase during SD correlated negatively with short-term neurological recovery (ECoG IQ 90 min post-ROSC). The scattering increase during SD may be attributed to dendritic beading, an indicator of the amount of neuronal damage.

Post-CA RP was characterized using AC-ECoG and optical imaging and RP-related parameters were correlated with neurological outcome. Upon resuscitation, a corresponding RP was detected with AC-ECoG, DC potential, and tissue scattering. Earlier onset time of this RP also correlated with better neurological recovery. Combining SD and RP onset times in a multiple linear regression model enabled prediction of 24-hr NDS with a sensitivity, specificity, and ROC AUC of 82%, 91%, and 0.91, respectively. In addition, the combination of RP onset and change in tissue scattering during SD separated low ECoG IQ rats and high ECoG IQ rats into separate clusters. Thus, less tissue scattering during CA-induced SD was linked with faster RP post-ROSC, which led to higher ECoG IQ 90 minutes post-ROSC. Therefore, the SD and RP features may provide ultra-early prognostic markers of neurological outcome for CA patients.

Earlier SD During CA May be Neuroprotective

Earlier SD may be neuroprotective in a model of transient global cerebral ischemia and reperfusion. Furthermore, correlations between baseline glucose and SD and RP onsets we observed as shown in FIGS. 9A-9C. Rats with higher levels of baseline glucose had later onsets of SD and RP, as well as lower 24-hr NDS. This result suggests that depletion of energy stores in the brain may trigger SD, and that if this process happens earlier during entry into CA, it may help lead to better neurological recovery post-CPR.

Early SD Reduces Periods of Mismatch Between CBF and Brain Metabolism During CA

FIG. 10 shows a mechanism by which early SD and RP may be neuroprotective in CA. In the presence of anoxia leading to global cerebral ischemia (e.g., CA), reduced oxygen metabolism and gas exchange in the brain during periods of low flow CBF may be related to the formation of harmful reactive oxygen species. Evidence for this can be found in several different measurement parameters. First, metrics related to total perfusion from start of ischemia/anoxia to onset of SD (AUC of MAP and CBF) are lower in animals that recovered better post-CPR. Second, the ratio of CBF to CMRO2 (an indicator of the cerebral perfusion-metabolism mismatch) was lower at SD in animals that recovered better after CPR. This may suggest that continued perfusion during hypo-metabolism and/or anoxia in the brain is detrimental.

Early RP May Mitigate Reperfusion Injury Following Resuscitation

During the transient period from ROSC to RP, reperfusion occurs without sufficient corresponding recovery of cerebral metabolic activity. Therefore, the brain may be unable to consume enough of the newly-available oxygen. Specifically, animals with less total CBF prior to RP have better outcome. As during entry into CA, a flow-metabolism mismatch may lead to reperfusion injury, potentially by formation of reactive oxygen species, worsening neurological recovery. This is supported by data that rats with worse neurological recovery had greater total perfusion (MAP AUC, CBF AUC) from ROSC to RP.

Without wishing to limit the present invention to a particular theory or mechanism, SD and repolarization appear to be an ultra-early biomarker of neurological outcome in the animal model of CA+CPR. For instance, the results show that during asphyxial cardiac arrest, earlier onset of spreading depolarization and less cerebral blood flow (CBF) may be associated with improved neurological outcome. After resuscitation, a slow repolarization was detected on ECoG as supported by DC and optical imaging. Thus, earlier repolarization and less CBF during repolarization may be associated with improved neurological outcome. In further embodiments, inducing CSD earlier during cardiac arrest may be of benefit to improve outcome.

Figures 11A, 11B:
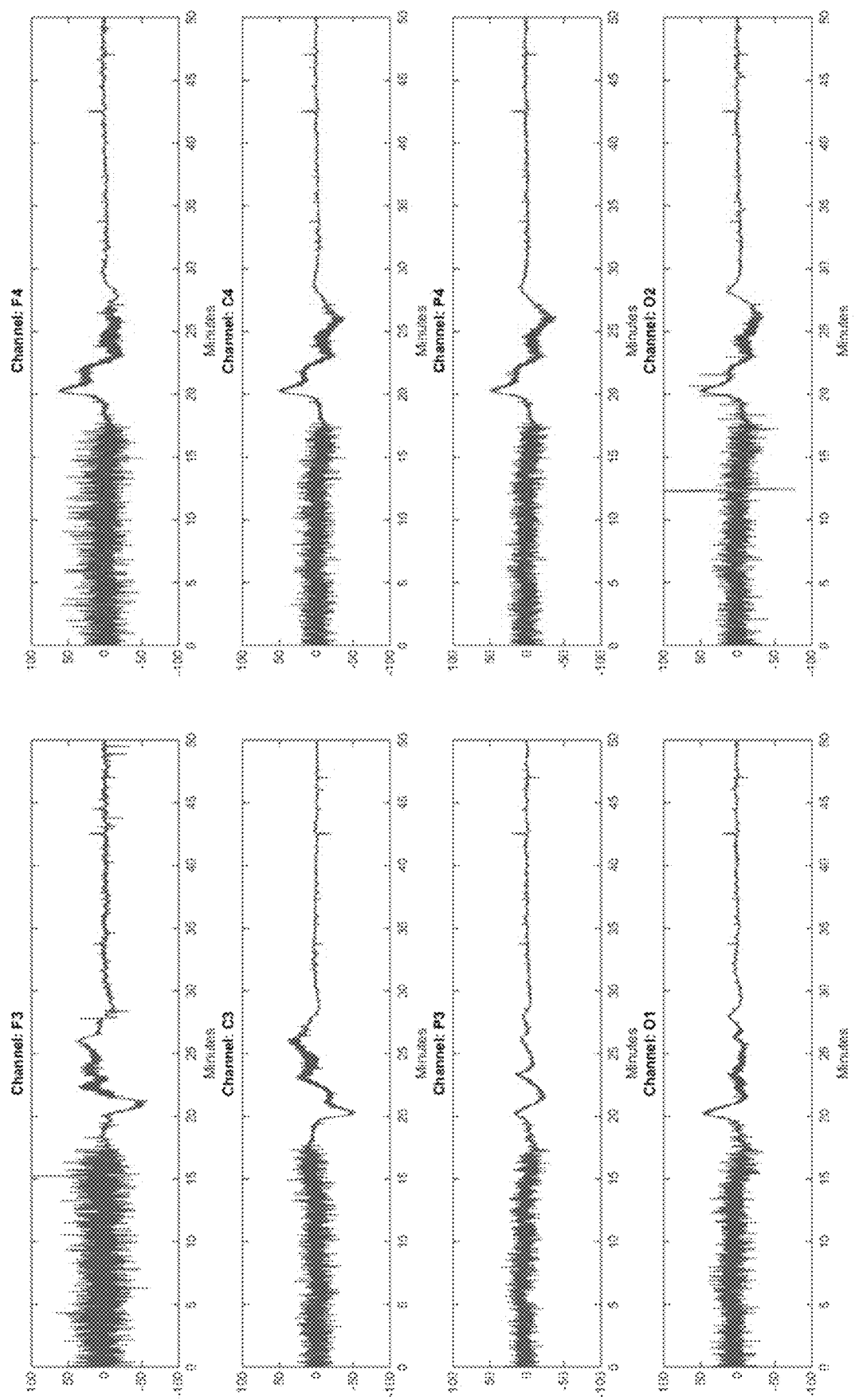
FIGS. 11A-11B show the detection of CSD in a patient using scalp EEG. Patient 1 (large wave at 20 minutes shows CSD) occurring within 2 minutes of cardiac arrest.
Figure 12:
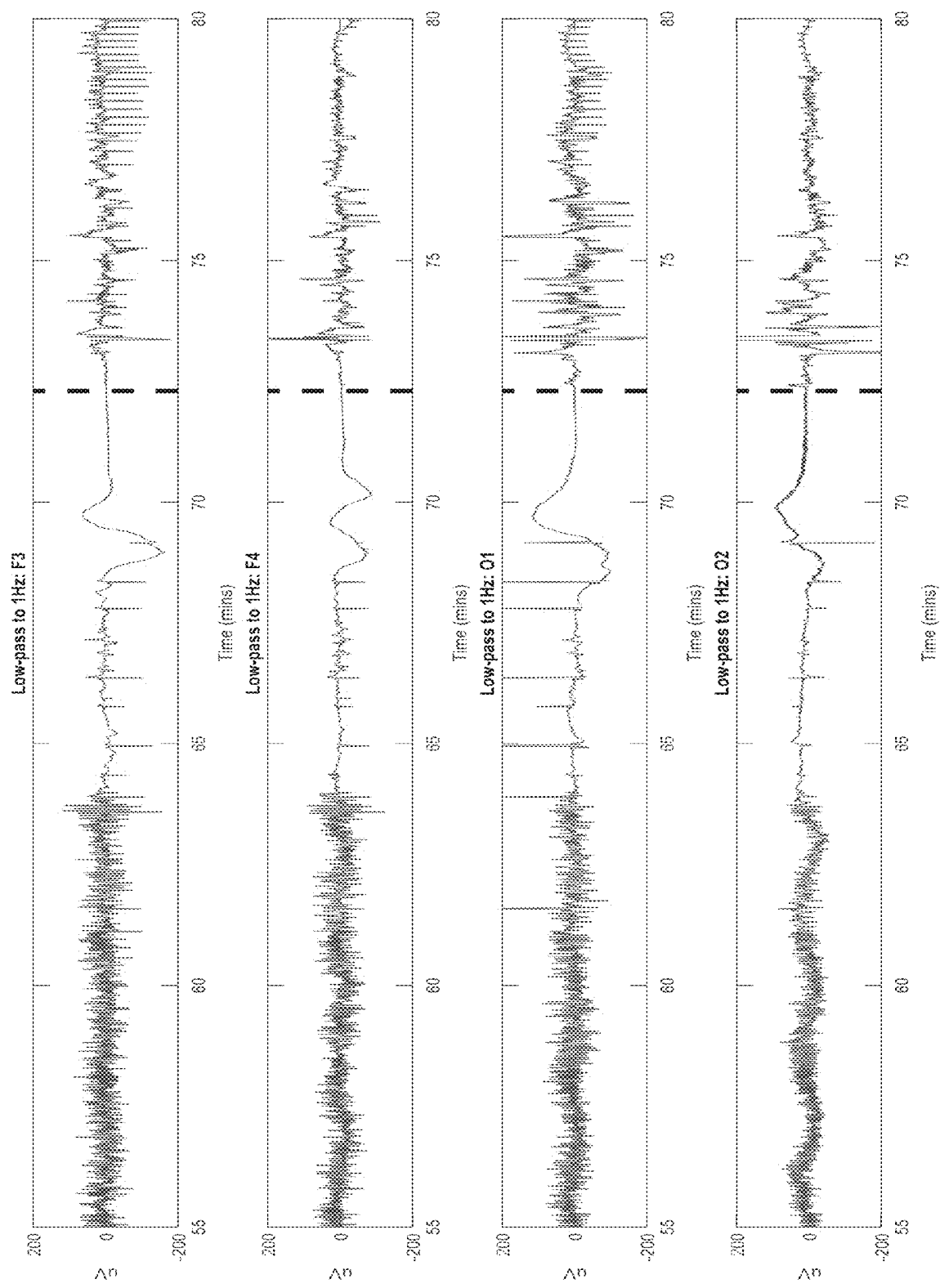
FIG. 12 demonstrates the detection of CSD in Patient #2 showing another CSD happening within 3-4 minutes of cardiac arrest, around minute 68.

In addition to the example above, at least two patients who suffered cardiac arrest at the UCI Medical Center while under EEG monitoring were identified. Referring to FIGS. 11A-11B and 12, the same type of electrophysiologic signals in the patients was investigated as a first-step translational bridge to the animal findings. The inventors have also identified what appeared to be CSD in the two patients, suggesting that this prognostic marker in animals may also apply to humans. The present discovery can have a huge impact on patients suffering CA in the hospital while under monitoring or if a monitor is quickly attached to them during CA or immediately after resuscitation. The latter is important, as paramedics and emergency clinical teams in the hospital can attach brain monitoring devices to patients suffering cardiac arrest.

Example 2. Determining Neurological Outcome of a Cardiac Arrest Patient

A 56 year old male patient is experiencing a drowning incident and is rescued by bystanders. The bystanders realize that the patient does not have a pulse and is suffering from a cardiac arrest. Bystanders immediately call for an automated external defibrillator (AED) as well as a portable EEG and optical device while CPR is initiated. The AED and EEG/optical device is brought to the patient. AED pads are applied to the patient's chest while EEG/optical device electrodes are rapidly applied to the head. While the AED informs the bystanders whether the cardiac rhythm is shockable or non-shockable, the EEG/optical device informs the bystanders if and when a SD event occurs in the brain. Paramedics arrive and CPR is continued. After 10 minutes of CPR, the patient regains a pulse and achieves return of spontaneous circulation. At this time, the EEG/optical device informs the bystanders and paramedics when an RP event occurs in the brain. The EEG/optical device also informs the paramedics about the CBF, tissue oxygenation, and CMRO2. The metrics arising from the brain may inform the paramedics to modulate treatments, such as raising the blood pressure via vasopressor medications or other medications that may modulate the cerebral blood flow or brain metabolism. The patient arrives to the hospital and the information about the SD onset, RP onset, tissue scattering change onset, tissue scattering change duration, and tissue scattering change magnitude are all relayed to the physicians, who in turn use this information to prognosticate the patient's potential recovery. The patient's prognosis (e.g. grim versus good) will be conveyed to the family to help them determine goals of care. Such an ultra-early prognostic marker will be very helpful for family as well as physicians to guide decisions and medical care.

Example 3. Improving Neurological Outcome of a Cardiac Arrest Patient

A 65 year old male patient is hospitalized for pneumonia. He has a history of heart disease and is at risk for a myocardial infarction (i.e. heart attack). On his $2^{nd}$ day of hospitalization, he suffers a myocardial infarction that results in a shockable cardiac arrest captured on the cardiac telemetry as a ventricular fibrillation. A "code blue" is called in the hospital while one nurse begins CPR and another nurse rapidly places AED pads on the chest and the EEG/optical device on the head. Physicians rapidly arrive to help while the AED indicates "shock needed" and the EEG/optical device on the head does not show any SD yet. The EEG/optical device has a built in feature using either electrical stimulation, magnetic stimulation, optical stimulation, soundwave-induced stimulation, or a combination thereof where an SD can be induced. The physician first "induces" an SD to the brain of the patient early in the course of the cardiac arrest incident using said device, which is immediately followed by a shock to the heart through the AED. CPR is continued and return of spontaneous circulation is achieved as the patient's cardiac rhythm is normalized and pulse is achieved. The RP is subsequently captured by the EEG/optical device, helping to prognosticate and guide further treatments.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of improving a neurological outcome in a subject during cardiac arrest, comprising:
   a. detecting spreading depolarization (SD), or a lack or delay of the SD, in a brain of the subject post cardiac arrest to generate SD data;
   b. resuscitating the subject;
   c. detecting repolarization (RP), or a lack or delay of the RP, in the brain of the subject post resuscitation to generate RP data;

d. comparing the SD and RP data to one or more metrics to determine a neurological outcome score;

e. identifying a neurological condition of the brain based on the neurological outcome score;

f. administering a treatment to the subject to improve the neurological condition of the brain; and g. determining severity and prognosticating the neurological outcome of the neurological condition using the neurological outcome score;

wherein the SD is a biomarker for the neurological outcome of the brain post-cardiac arrest, wherein the RP is a biomarker for the neurological outcome of the brain post-resuscitation, and wherein prognosticating the neurological outcome of the neurological condition of the brain is determined in real-time.

2. The method of claim 1, wherein the treatment comprises therapeutically administering a drug, electrical stimulation, magnetic stimulation, optical stimulation, soundwave-induced stimulation, or a combination thereof.

3. The method of claim 1 further comprising:

a. measuring one or more of cerebral blood flow (CBF), tissue oxygenation, and tissue scattering in the brain;

b. determining one or more of cerebral metabolic rate of oxygen (CMRO2) from the measurements of the CBF and the tissue oxygenation, and scattering change onset, duration, and magnitude of the scattering change; and c. comparing one or more of the CMRO2, the scattering change onset, the duration of scattering change, the magnitude of scattering change, the CBF measurements, and the tissue oxygenation measurements to one or more metrics to determine the neurological outcome score.

4. The method of claim 3, wherein one or more of the CBF, tissue oxygenation, and tissue scattering are measured by one or more optical measurement devices comprising point measurement devices, diffuse optical measurement devices, or optical measurement devices capable of measuring one or more of the CBF, tissue oxygenation, and tissue scattering through intact human skull.

5. The method of claim 1, wherein the SD and RP are detected by an electroencephalogram (EEG), an electrocorticograph (ECoG), one or more optical measurement devices, or a combination thereof.

6. The method of claim 1 further comprising inducing the SD in the brain during or immediately after the cardiac arrest.

7. The method of claim 1 further comprising inducing the RP in the brain during or immediately after the resuscitation.

* * * * *